US012653658B2

(12) United States Patent
Sholev et al.

(10) Patent No.: US 12,653,658 B2
(45) Date of Patent: Jun. 16, 2026

(54) FIXATING MEANS BETWEEN A MESH AND MESH DEPLOYMENT MEANS ESPECIALLY USEFUL FOR HERNIA REPAIR SURGERIES AND METHODS THEREOF

(71) Applicant: Davol Inc., Warwick, RI (US)

(72) Inventors: Mordehai Sholev, Menashe (IL); Ruth Zajdman, Haifa (IL); Itay Ben-Nun, Carmiel (IL)

(73) Assignee: Davol Inc., Warwick, RI (US)

( * ) Notice: Subject to any disclaimer, the term of this patent is extended or adjusted under 35 U.S.C. 154(b) by 209 days.

(21) Appl. No.: 18/476,139

(22) Filed: Sep. 27, 2023

(65) Prior Publication Data

US 2024/0090991 A1     Mar. 21, 2024

Related U.S. Application Data

(63) Continuation of application No. 16/934,939, filed on Jul. 21, 2020, now Pat. No. 11,806,223, which is a
(Continued)

(51) Int. Cl.
*A61F 2/00*          (2006.01)
(52) U.S. Cl.
CPC .... *A61F 2/0063* (2013.01); *A61F 2002/0072* (2013.01)
(58) Field of Classification Search
CPC ........................ A61F 2/0063; A61F 2023/0072
See application file for complete search history.

(56) References Cited

U.S. PATENT DOCUMENTS

| 460,940 A | 10/1891 | Baugii |
| 3,857,395 A | 12/1974 | Johnson et al. |
| | (Continued) | |

FOREIGN PATENT DOCUMENTS

| EP | 0 557 963 A1 | 9/1993 |
| EP | 1 336 391 A1 | 8/2003 |
| | (Continued) | |

OTHER PUBLICATIONS

Extended European Search Report dated Aug. 21, 2012 for European Application No. 08839227.9.
(Continued)

*Primary Examiner* — Dianne Dornbusch
(74) *Attorney, Agent, or Firm* — Wolf, Greenfield & Sacks, P.C.

(57) ABSTRACT

The present invention provides a fixating means adapted for use in hernia repair surgeries in attaching a mesh and mesh deployment means; said fixating means are attached to said mesh deployment means; and fixating means comprising: (a) a first portion coupled to said deployment means; and, (b) a second portion comprising a coil having a predetermined retracted shape; said coil is reconfigurable from a plurality of unretracted positions to a plurality of retracted positions and from said plurality of retracted positions to said plurality of unretracted positions; wherein said attachment between said deployment means and said mesh is obtained by reconfiguration of said coil from at least one of said unretracted positions to at least one of said retracted positions.

20 Claims, 22 Drawing Sheets

Related U.S. Application Data continuation of application No. 15/476,822, filed on Mar. 31, 2017, now Pat. No. 10,751,156, which is a continuation of application No. 13/921,921, filed on Jun. 19, 2013, now Pat. No. 9,642,689, which is a continuation of application No. 12/738,454, filed as application No. PCT/IL2008/001381 on Oct. 22, 2008, now Pat. No. 8,500,762.

(60) Provisional application No. 60/960,860, filed on Oct. 17, 2007.

(56) References Cited

U.S. PATENT DOCUMENTS

| | | | |
|---|---|---|---|
| 3,863,639 A | 2/1975 | Kleaveland | |
| 3,874,388 A | 4/1975 | King et al. | |
| 4,055,861 A | 11/1977 | Carpentier et al. | |
| 4,685,447 A | 8/1987 | Iversen et al. | |
| 4,705,041 A * | 11/1987 | Kim | A61M 29/00 |
| | | | 606/198 |
| 4,769,038 A | 9/1988 | Bendavid et al. | |
| 4,823,815 A | 4/1989 | Watson et al. | |
| 5,011,481 A | 4/1991 | Myers et al. | |
| 5,116,357 A | 5/1992 | Eberlach | |
| 5,176,692 A | 1/1993 | Wilk | |
| 5,263,969 A | 11/1993 | Phillips | |
| 5,308,327 A | 5/1994 | Heaven et al. | |
| 5,309,896 A | 5/1994 | Moll et al. | |
| 5,333,624 A | 8/1994 | Tovey | |
| 5,350,388 A | 9/1994 | Epstein | |
| 5,361,752 A | 11/1994 | Moll et al. | |
| 5,366,460 A | 11/1994 | Eberbach | |
| 5,370,650 A | 12/1994 | Tovey et al. | |
| 5,395,383 A | 3/1995 | Adams et al. | |
| 5,397,332 A * | 3/1995 | Kammerer | A61B 17/0057 |
| | | | 606/198 |
| 5,405,360 A | 4/1995 | Tovey | |
| 5,496,345 A | 3/1996 | Kieturakis et al. | |
| 5,527,264 A | 6/1996 | Moll et al. | |
| 5,575,759 A | 11/1996 | Moll et al. | |
| 5,607,443 A | 3/1997 | Kierturakis | |
| 5,695,498 A | 12/1997 | Tower | |
| 5,702,416 A | 12/1997 | Kierturakis | |
| 5,743,851 A | 4/1998 | Moll et al. | |
| 5,769,864 A | 6/1998 | Kugel | |
| 5,797,960 A | 8/1998 | Stevens et al. | |
| 5,824,082 A | 10/1998 | Brown | |
| 5,836,871 A | 11/1998 | Wallace et al. | |
| 5,836,961 A | 11/1998 | Kierturakis | |
| 5,871,498 A | 2/1999 | Jervis et al. | |
| 5,957,939 A | 9/1999 | Heaven et al. | |
| 6,168,608 B1 | 1/2001 | Echeverry et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,224,616 B1 | 5/2001 | Kugel | |
| 6,258,113 B1 | 7/2001 | Adams et al. | |
| 6,302,897 B1 | 10/2001 | Rousseau | |
| 6,312,442 B1 | 11/2001 | Kierturakis | |
| 6,379,368 B1 | 4/2002 | Corcoran et al. | |
| 6,488,653 B1 | 12/2002 | Lombardo | |
| 6,551,241 B1 | 4/2003 | Schultz | |
| 6,565,590 B2 | 5/2003 | Kierturakis et al. | |
| 6,575,988 B2 | 6/2003 | Rousseau | |
| 6,638,292 B2 | 10/2003 | Adams | |
| 6,663,647 B2 | 12/2003 | Reiley et al. | |
| 6,679,900 B2 | 1/2004 | Kierturakis | |
| 6,685,714 B2 | 2/2004 | Rousseau | |
| 6,702,827 B1 | 3/2004 | Lund et al. | |
| 6,755,868 B2 | 6/2004 | Rousseau | |
| 6,866,676 B2 | 3/2005 | Kierturakis | |
| 6,913,614 B2 | 7/2005 | Marino et al. | |
| 7,048,698 B2 | 5/2006 | Whalen et al. | |
| 7,101,381 B2 | 9/2006 | Ford et al. | |
| 7,128,073 B1 | 10/2006 | van der Burg et al. | |
| 7,235,042 B2 | 6/2007 | Vanden Hoek et al. | |
| 7,273,489 B2 | 9/2007 | Boudjemline | |
| 7,544,213 B2 | 6/2009 | Adams | |
| 7,678,123 B2 | 3/2010 | Chanduszko | |
| 7,744,617 B2 | 6/2010 | Lunsford et al. | |
| 7,780,683 B2 | 8/2010 | Roue et al. | |
| 7,947,054 B2 | 5/2011 | Eldar et al. | |
| 8,007,502 B2 | 8/2011 | Chu et al. | |
| 8,016,851 B2 | 9/2011 | Dillon et al. | |
| 8,043,381 B2 | 10/2011 | Hestad et al. | |
| 8,372,112 B2 | 2/2013 | Christianson et al. | |
| 8,382,796 B2 | 2/2013 | Blaeser et al. | |
| 8,500,762 B2 | 8/2013 | Sholev et al. | |
| 8,920,370 B2 | 12/2014 | Sholev et al. | |
| 8,920,445 B2 | 12/2014 | Sholev | |
| 9,439,643 B2 | 9/2016 | Darois et al. | |
| 9,504,548 B2 | 11/2016 | Darois et al. | |
| 9,642,689 B2 | 5/2017 | Sholev et al. | |
| 9,687,332 B2 | 6/2017 | Sholev et al. | |
| 9,808,331 B2 | 11/2017 | Felix et al. | |
| 9,861,462 B2 | 1/2018 | Sholev et al. | |
| 9,993,324 B2 | 6/2018 | Sholev | |
| 10,166,093 B2 | 1/2019 | Felix et al. | |
| 10,548,703 B2 | 2/2020 | Darois et al. | |
| 10,751,156 B2 | 8/2020 | Sholev et al. | |
| 10,864,068 B2 | 12/2020 | Sholev | |
| 10,898,309 B2 | 1/2021 | Sholev et al. | |
| 10,905,537 B2 | 2/2021 | Felix et al. | |
| 2001/0053919 A1 | 12/2001 | Kieturakis et al. | |
| 2002/0133236 A1 | 9/2002 | Rousseau | |
| 2003/0004581 A1 | 1/2003 | Rousseau | |
| 2003/0187472 A1 | 10/2003 | Peartree et al. | |
| 2003/0236544 A1 | 12/2003 | Lunsford et al. | |
| 2004/0073257 A1 | 4/2004 | Spitz | |
| 2004/0087980 A1 | 5/2004 | Ford et al. | |
| 2004/0092970 A1 | 5/2004 | Xavier | |
| 2004/0097792 A1 | 5/2004 | Moll et al. | |
| 2004/0167557 A1 | 8/2004 | Kieturakis et al. | |
| 2004/0172048 A1 | 9/2004 | Browning | |
| 2004/0236363 A1 | 11/2004 | Kieturakis | |
| 2005/0033318 A1 | 2/2005 | Miller | |
| 2005/0049635 A1 | 3/2005 | Leiboff | |
| 2005/0059854 A1 | 3/2005 | Hoek et al. | |
| 2005/0171569 A1 | 8/2005 | Girard et al. | |
| 2006/0106418 A1 | 5/2006 | Seibold et al. | |
| 2006/0247586 A1 | 11/2006 | Voegele et al. | |
| 2007/0066980 A1 * | 3/2007 | Leahy | A61B 17/0057 |
| | | | 606/151 |
| 2007/0078477 A1 | 4/2007 | Heneveld et al. | |
| 2007/0100369 A1 | 5/2007 | Cragg et al. | |
| 2007/0185506 A1 * | 8/2007 | Jackson | A61F 2/0063 |
| | | | 606/151 |
| 2007/0260179 A1 | 11/2007 | Sholev et al. | |
| 2008/0033461 A1 | 2/2008 | Koeckerling et al. | |
| 2008/0065229 A1 | 3/2008 | Adams | |
| 2008/0147200 A1 | 6/2008 | Rousseau et al. | |
| 2008/0167729 A1 | 7/2008 | Nelson et al. | |
| 2008/0195121 A1 | 8/2008 | Eldar et al. | |
| 2009/0012350 A1 | 1/2009 | Tihon | |
| 2009/0082792 A1 | 3/2009 | Koyfman et al. | |
| 2009/0192605 A1 | 7/2009 | Gloss et al. | |
| 2009/0254103 A1 | 10/2009 | Deutsch | |
| 2009/0287046 A1 | 11/2009 | Yamatani | |
| 2010/0069947 A1 * | 3/2010 | Sholev | A61F 2/0063 |
| | | | 606/192 |
| 2010/0137999 A1 | 6/2010 | Shohat | |
| 2010/0292718 A1 | 11/2010 | Sholev et al. | |
| 2010/0318121 A1 | 12/2010 | Levin et al. | |
| 2011/0112560 A1 | 5/2011 | Sholev | |
| 2011/0295283 A1 | 12/2011 | Darois et al. | |
| 2012/0109179 A1 | 5/2012 | Murphy et al. | |
| 2013/0218179 A1 | 8/2013 | Sholev et al. | |
| 2013/0231526 A1 | 9/2013 | Felix et al. | |
| 2014/0051915 A1 | 2/2014 | Sholev et al. | |
| 2015/0196377 A1 | 7/2015 | Sholev et al. | |
| 2015/0202035 A1 | 7/2015 | Sholev | |
| 2017/0100229 A1 | 4/2017 | Darois et al. | |
| 2017/0290577 A1 | 10/2017 | Sholev et al. | |

(56)                    References Cited

U.S. PATENT DOCUMENTS

| | | | |
|---|---|---|---|
| 2018/0092725 | A1 | 4/2018 | Felix et al. |
| 2018/0147040 | A1 | 5/2018 | Sholev et al. |
| 2018/0368962 | A1 | 12/2018 | Sholev |
| 2019/0151066 | A1 | 5/2019 | Felix et al. |
| 2021/0045862 | A1 | 2/2021 | Sholev et al. |
| 2021/0128289 | A1 | 5/2021 | Sholev |
| 2021/0169628 | A1 | 6/2021 | Sholev et al. |
| 2021/0169629 | A1 | 6/2021 | Felix et al. |

FOREIGN PATENT DOCUMENTS

| | | | |
|---|---|---|---|
| EP | 1 454 599 | A2 | 9/2004 |
| GB | 2397239 | A | 7/2004 |
| JP | 2000-501634 | A | 2/2000 |
| JP | 2007-275203 | A | 10/2007 |
| JP | 2008-520372 | A | 6/2008 |
| WO | WO 95/30374 | A1 | 11/1995 |
| WO | WO 96/00531 | A1 | 1/1996 |
| WO | WO 97/21461 | A1 | 6/1997 |
| WO | WO 2005/046511 | A2 | 5/2005 |
| WO | WO 2006/040760 | A2 | 4/2006 |
| WO | WO 2006/055823 | A2 | 5/2006 |
| WO | WO 2007/030676 | A2 | 3/2007 |
| WO | WO 2007/115110 | A2 | 10/2007 |
| WO | WO 2008/045635 | A2 | 4/2008 |
| WO | WO 2008/065653 | A1 | 6/2008 |
| WO | WO 2009/050717 | A2 | 4/2009 |

OTHER PUBLICATIONS

Extended European Search Report dated Jun. 12, 2014 for European Application No. 14161232.5.

Extended European Search Report dated Jan. 20, 2016 for European Application No. 15189404.5.

Extended European Search Report dated Sep. 5, 2017 for European Application No. 17167634.9.

International Search Report and Written Opinion mailed Mar. 16, 2009 for International Application No. PCT/IL2008/001381.

International Preliminary Report on Patentability mailed Apr. 29, 2010 for International Application No. PCT/IL2008/001381.

* cited by examiner

252

252

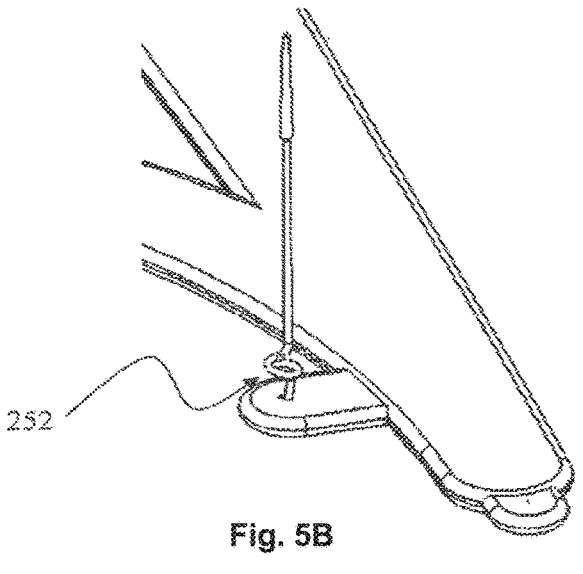
252
Fig. 5B
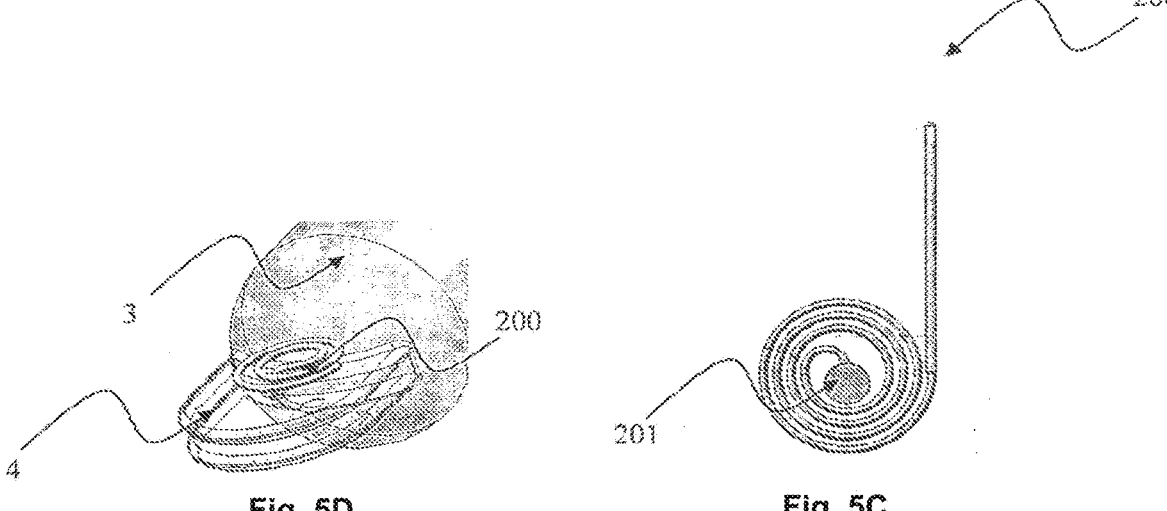
200
3
200
4
201
Fig. 5D
Fig. 5C

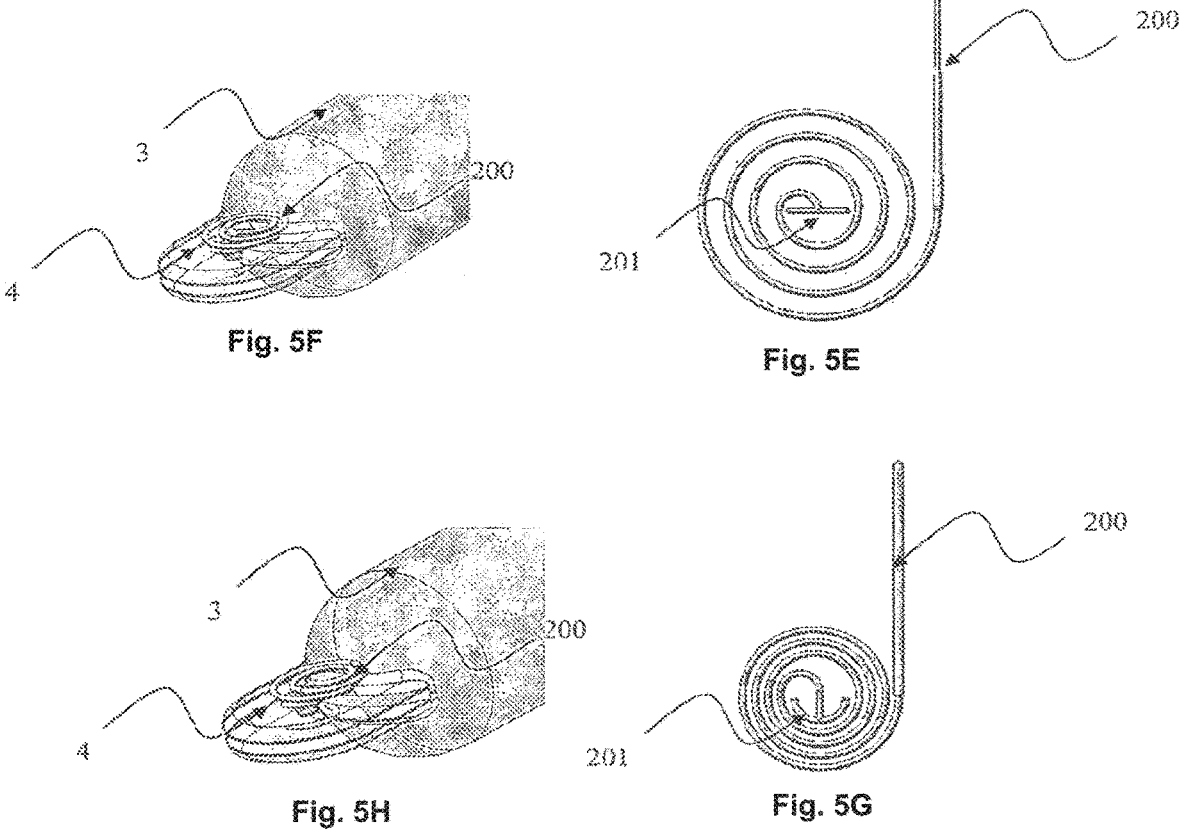
Fig. 5F
Fig. 5E
Fig. 5H
Fig. 5G
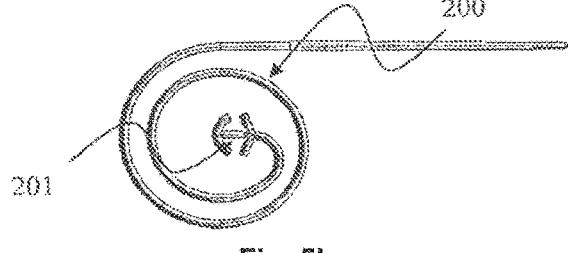
Fig. 5I

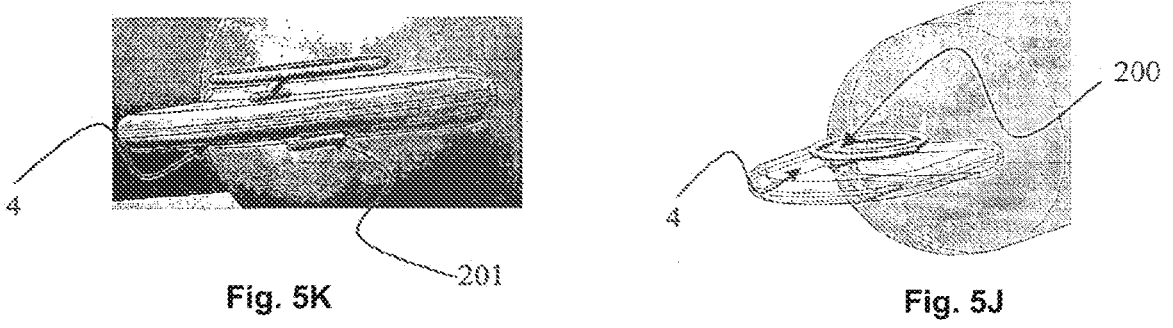
Fig. 5K
Fig. 5J
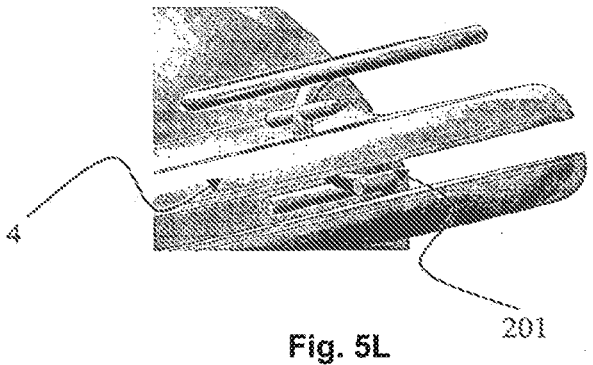
Fig. 5L

700 obtaining a hernia kit
702 threading the sharpened element through the patch/mesh
703 pulling the stylet through the patch/mesh
704 reconfiguring said coil from unretracted position (linear shape) into its retracted configuration (e.g., helical configuration)
705 detaching the stylete
706

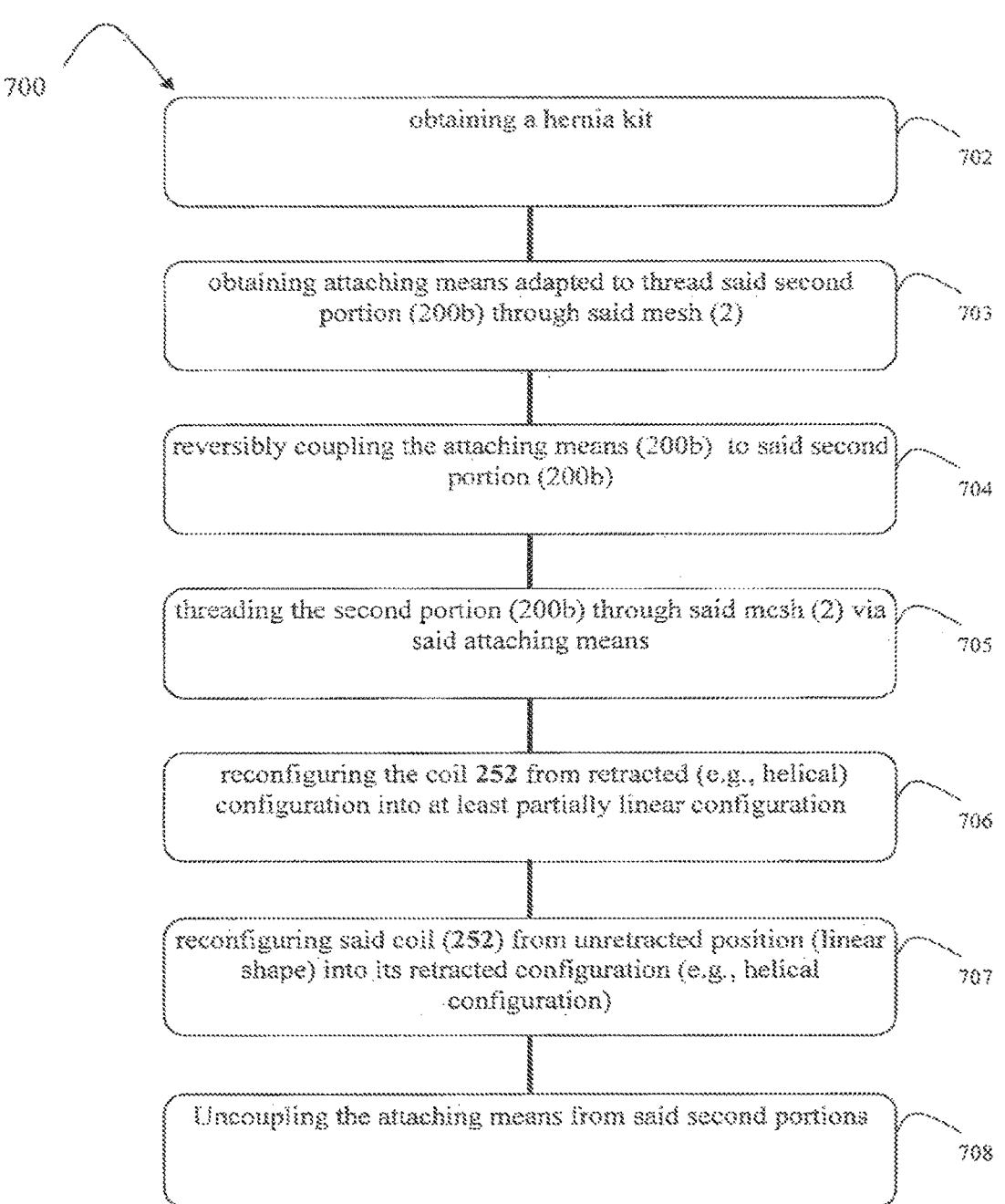

700 obtaining a hernia kit

702 obtaining attaching means adapted to thread said second
portion (200b) through said mesh (2)

703 reversibly coupling the attaching means (200b) to said second
portion (200b)

704 threading the second portion (200b) through said mesh (2) via
said attaching means

705 reconfiguring the coil 252 from retracted (e.g., helical)
configuration into at least partially linear configuration

706 reconfiguring said coil (252) from unretracted position (linear
shape) into its retracted configuration (e.g., helical
configuration)

707

Uncoupling the attaching means from said second portions

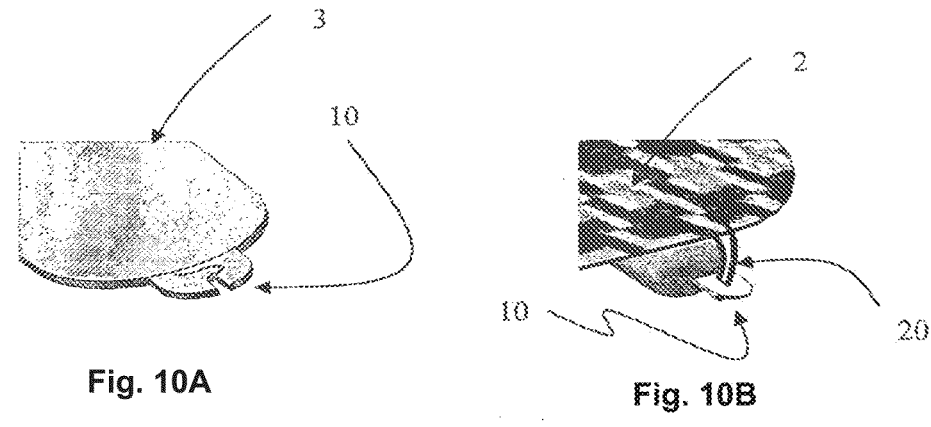
Fig. 10A                    Fig. 10B
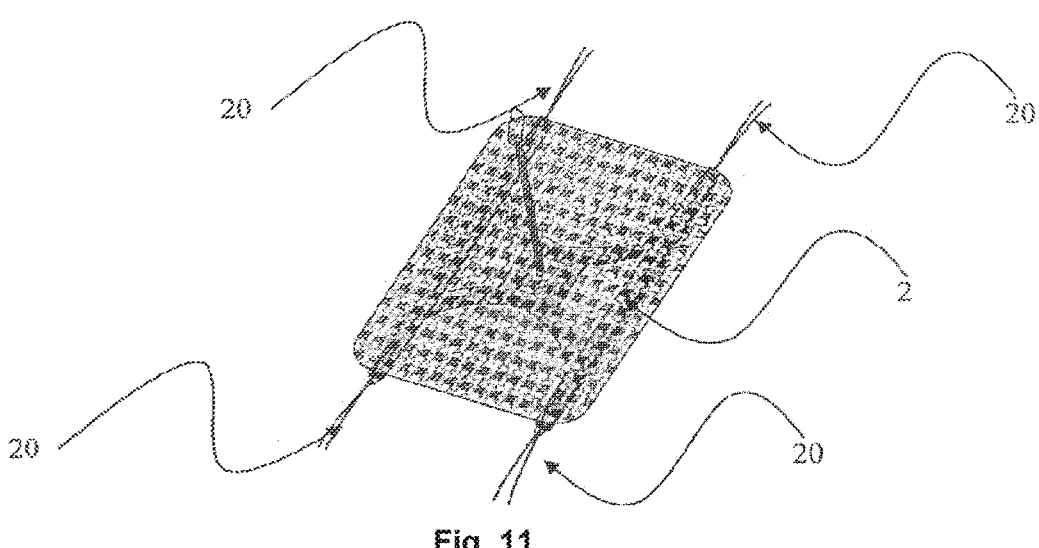
Fig. 11

2

FIXATING MEANS BETWEEN A MESH AND MESH DEPLOYMENT MEANS ESPECIALLY USEFUL FOR HERNIA REPAIR SURGERIES AND METHODS THEREOF

CROSS-REFERENCE TO RELATED APPLICATIONS

This Application is a Continuation of U.S. application Ser. No. 16/934,939, filed Jul. 21, 2020, which is a Continuation of U.S. application Ser. No. 15/476,822, filed Mar. 31, 2017, now U.S. Pat. No. 10,751,156, which is a Continuation of U.S. application Ser. No. 13/921,921, filed Jun. 19, 2013, now U.S. Pat. No. 9,642,689, which is a Continuation of U.S. application Ser. No. 12/738,454, filed Aug. 4, 2010, now U.S. Pat. No. 8,500,762, which is a national stage filing under 35 U.S.C. 371 of International Patent Application Serial No. PCT/IL2008/001381, filed Oct. 22, 2008, which claims the benefit of U.S. Application Ser. No. 60/960,860, filed Oct. 17, 2007. The entire contents of these applications are incorporated herein by reference.

FIELD OF THE INVENTION

This invention generally relates to fixating means between a hernia repair mesh and a mesh deployment means used to deploy the mesh, especially useful for hernia repair surgery.

BACKGROUND

This invention generally relates to an inflatable balloon and/or other mesh deployment means, especially useful for hernia repair surgery.

Modern surgical techniques are intended to be minimally invasive. Endoscopic surgery is a prime example of this minimally invasive approach and has led to the development of various instruments that may be inserted through a small incision to operate internally. Minimally invasive procedures are also commonly employed in the treatment of hernia (inguinal, femoral, hiatal, ventral, incisional and umbilical hernias).

Hernia is a common medical condition in which an organ protrudes through an opening in its surrounding tissue (especially in the abdominal region). The hernia is sometimes treated in a tension free repair, such as implementation of meshes/patches. In carrying out laparoscopic ventral or incisional or umbilical or inguinal hernia procedures, the surgeon usually rolls the patch/mesh and then inserts it into a trocar sleeve or its opening and delivers it into the abdominal or pre-peritoneal cavity. A laparoscopic forceps is then used to unfurl the mesh/patch and place it posterior to the hernia defect completely covering it with a sufficient overlap. The mesh/patch may then be held in place by stapling or suturing it to underlying tissue.

One of the major problems of the above procedure is the unrolling or spreading and the positioning or deploying of the mesh inside the abdominal or the pre-peritoneal cavity. The step of unrolling the mesh, directing the right side of the mesh and it's orientation, positioning and fixating the mesh and positioning it in the right place and orienting it to the right direction, usually adds significantly to the time required for carrying out the procedure.

U.S. Pat. No. 5,824,082 ('082) relates to a prosthetic hernia repair patch that can be rolled into a tube for laparoscopic delivery through a trocar and which deploys to a generally planar form when ejected from the trocar into the abdominal cavity. The deployment of the prosthetic is done by embedding a wire frame made of shape memory alloys into the prosthetic. When the prosthetic is inserted into the body it is heated thus, activated—i.e. it springs into its functional, predetermined configuration and deploys the patch. However, embedding a wire frame in a prosthetic is complicated.

Another approach to the problem of folds in a deployed mesh was to attach it to an inflatable balloon which, after inflation, expands and spreads the mesh. Such a device was disclosed in PCT publication no. WO08/065653. It was found that the fixation of the mesh to the inflatable balloon is of utmost importance, since a method of connecting and disconnecting should be stand specific standards. It should not only allow a rapid fixation, but also, if necessary, rapid disconnection. The user should be able to perform the fixation and the disconnection not only outside the body, but also in a narrow abdominal cavity, during an open and even a laparoscopic procedure. Despite the required detachment abilities, the fixation should be strong as long as it is required, so that the mesh, deployed under laparoscopic measures, won't detach or fold in the abdominal cavity. The fixation should not harm the inflatable balloon or the mesh, and should allow the fixation of different sizes of meshes to different sizes of balloons, so as not to limit the options.

Thus, there is still a long felt need for a device that, is simple and will shorten the time required for the spreading and the positioning of the mesh inside the body.

Furthermore, there is still need for a device that can strongly fixate a variety of mesh sizes to an inflatable balloon, or other deployment means, with rapid and easy attachment/detachment capabilities even under laparoscopic procedure, without damaging the patient, the mesh or the balloon.

SUMMARY OF THE INVENTION

It is one object of the present invention to provide a hernia kit useful in minimal invasive and/or open surgery, comprising:

a. a mesh (2);

b. at least one deployment means (3), adapted to deploy said mesh within the abdominal cavity and/or pre-peritoneal and/or hollow body organs and/or natural and/or artificial orifices and/or spaces and/or post operative spaces; and, c. fixating means (200) coupled to said deployment means (3), adapted to attach said deployment means (3) to said mesh (2), said fixating means are characterized by at least two portions:

i. a first portion (200*a*) coupled to said deployment means (3); and, ii. a second portion (200*b*), comprising a coil (252) having a predetermined retracted shape; said coil is reconfigurable from a plurality of unretracted positions to a plurality of retracted positions and from said plurality of retracted positions to said plurality of unretracted positions;

wherein said attachment between said deployment means (3) and said mesh (2) is obtained by reconfiguration of said coil (252) from at least one of said unretracted positions to at least one of said retracted positions.

It is another object of the present invention to provide the hernia kit as defined above, wherein said deployment means (3) is an inflatable balloon.

It is another object of the present invention to provide the hernia kit as defined above, wherein said fixating means additionally comprising means reversibly coupled to said second portion, adapted to thread said second portion (200*b*) through said mesh (2).

It is another object of the present invention to provide the hernia kit as defined above, wherein said fixating means additionally comprising a third portion (200*c*) having at least one sharpened element (256), adapted to fully penetrate said mesh (2).

It is another object of the present invention to provide the hernia kit as defined above, wherein said fixating means (200) are coupled to said deployment means (3) by means selected from a group consisting of glue, Velcro, mechanical connections selected from a group consisting of a disc or a knot, welding means, threading means or any combination thereof.

It is another object of the present invention to provide the hernia kit as defined above, wherein said unretracted position is at least partially linear configuration.

It is another object of the present invention to provide the hernia kit as defined above, wherein said coil is made of materials selected from a group consisting of nylon, shape memory materials, Thermoplastic materials, Polyurethane, EAP, biodegradable materials or any combination thereof.

It is another object of the present invention to provide the hernia kit as defined above, wherein said deployment means (3) is made of materials selected from a group consisting of nylon, shape memory materials, Thermoplastic materials, Polyurethane, EAP, biodegradable materials, stainless steel, other metals, plastic or any combination thereof.

It is another object of the present invention to provide the hernia kit as defined above, wherein said coil is a coaxial structure, comprising at least partially a helical and/or spiral shape, such that said structure can be unretracted to a more linear shape and retracted back to at least partially a helical and/or spiral shape.

It is another object of the present invention to provide the hernia kit, as defined above, wherein said coil is a coaxial structure, comprising an outer cannula with a longitudinal slit and an inner thread, such that said cannula collapses into a helical configuration after said inner thread is pulled out.

It is another object of the present invention to provide the hernia kit as defined above, wherein said coil is reconfigurable from a retracted position to an unretracted position by means selected from a group consisting of mechanically pulling or pushing said coil, applying electrical current on said coil, thermoregulating said coil, applying magnetic field.

It is another object of the present invention to provide the hernia kit as defined above, wherein said coil is spontaneously reconfigurable from a retracted position to an unretracted position.

It is another object of the present invention to provide the hernia kit as defined above, wherein said coil has at least one coiling radius.

It is another object of the present invention to provide the hernia kit as defined above, wherein said sharpened element is selected from a group consisting of a stylet or a needle.

It is another object of the present invention to provide the hernia kit as defined above, wherein said deployment means (3) additionally comprising at least one appendage to which said first portion of said fixating means (200) is coupled.

It is another object of the present invention to provide the hernia kit as defined above, wherein said first portion (200*a*) of said fixating means (200) is coupled to various locations on said deployment means (3), thus accommodating a variety of mesh sizes.

It is another object of the present invention to provide the hernia kit as defined above, wherein said deployment means (3) is in communication with inflating means adapted to inflate said deployment means (3).

It is another object of the present invention to provide the hernia kit as defined above, wherein the shape of said deployment means is selected from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, an shape, a grid-like shape, a flat structure, a 3D structure and a rake-like shape or any combination thereof.

It is another object of the present invention to provide the hernia kit as defined above, wherein said deployment means additionally comprising centering means adapted to adjust the center of said deployment means and said mesh to the center of said hernia.

It is another object of the present invention to provide the hernia kit as defined above, wherein said deployment means additionally comprising means adapted to ensure the right side of said mesh is directed to said hernia.

It is another object of the present invention to provide the hernia kit as defined above, wherein said deployment means additionally comprising means adapted to ensure the right direction of said mesh in the abdominal cavity.

It is another object of the present invention to provide the hernia kit as defined above, wherein said centering means additionally comprising means adapted to thread said centering means through said mesh.

It is another object of the present invention to provide the hernia kit as defined above, wherein said deployment means additionally comprising at least one clip adapted to grab sutures.

It is another object of the present invention to provide the hernia kit as defined above, wherein said centering means additionally comprising means (9) adapted to enable the grasp of said centering means with a surgical tool.

It is another object of the present invention to provide a method for attaching a mesh to deployment means, comprising steps selected inter alia from of:
  a. obtaining a hernia kit comprising:
    i. a mesh (2);
    ii. at least one deployment means (3), adapted to deploy said mesh with in the abdominal cavity and/or pre-peritoneal and/or hollow body organs and/or natural and/or artificial orifices and/or spaces and/or post operative spaces; and,
    iii. fixating means (200) coupled to said deployment means (3), adapted to attach said deployment means (3) to said mesh (2); said fixating means are characterized by:
      a. a proximal portion (200*a*) coupled to said deployment means (3);
      b. a middle portion (200*b*), comprising a coil (252) having a predetermined retracted shape; said coil is reconfigurable from a plurality of unretracted positions to a plurality of retracted positions and from said plurality of retracted positions to said plurality of unretracted positions; and,
      c. a distal portion (200*c*) comprising at least one sharpened element (256), adapted to fully penetrate said mesh (2);
  b. threading said sharpened element (256) through said mesh (2);

c. reconfiguring said coil (252) from said retracted position to an unretracted position; thereby at least partially passing said coil through said mesh; and, d. reconfiguring said coil (252) from said unretracted position to said retracted position thereby attaching said mesh to said deployment means.

It is another object of the present invention to provide the method as defined above, additionally comprising step of selecting said deployment, means from a group consisting of inflatable balloon.

It is another object of the present invention to provide the method as defined above, additionally comprising step of cutting said distal portion of said fixating means (200), thereby removing said sharpened element (256).

It is another object of the present invention to provide the method as defined above, additionally comprising steps of (a) adjusting said mesh attached to said deployment means; and, (b) inserting said adjusted deployment means attached to said mesh into the abdominal cavity and/or pre-peritoneal and/or hollow body organs and/or natural and/or artificial orifices and/or spaces and/or post operative spaces.

It is another object of the present invention to provide the method as defined above, additionally comprising step spreading and/or deploying said mesh.

It is another object of the present invention to provide the method as defined above, wherein said step spreading and/or deploying said mesh additionally comprising step of inflating at least a portion of said deployment, means or actuating at least a part of the deployment means.

It is another object of the present invention to provide the method as defined above, additionally comprising step of coupling said fixating means (200) to said deployment means (3) by means selected from a group consisting of glue, Velcro, mechanical connections selected from a group consisting of a disc or a knot), welding means, threading or any combination thereof.

It is another object of the present invention to provide the method as defined above, wherein said step (c) of reconfiguring said coil from said retracted position to an unretracted position additionally comprising step of mechanically pulling said coil.

It is another object of the present invention to provide the method as defined above, wherein said step (d) of reconfiguring said coil unretracted position to said retracted position additionally comprising step of releasing said mechanical stress.

It is another object of the present invention to provide the method as defined above, wherein said step (c) or said step (d) of reconfiguring said coil is performed by means selected from a group consisting of application of electrical current on said coil, thermoregulating said coil, application of magnetic field on said coil.

It is another object of the present invention to provide the method as defined above, wherein said step (d) of reconfiguring said coil unretracted position to said retracted position is performed spontaneously.

It is another object of the present invention to provide the method as defined above, wherein said step of step (c) of reconfiguring said coil from said retracted position to an unretracted position additionally comprising step of transforming said coil to a more linear configuration.

It is another object of the present invention to provide the method as defined above, wherein said step (d) of reconfiguring said coil unretracted position to said retracted position additionally comprising step of transforming said coil to at least partially a helical and/or spiral configuration.

It is another object of the present invention to provide the method as defined above, additionally comprising step of selecting said coil to have more than one coiling radius.

It is another object of the present invention to provide the method as defined above, additionally comprising step of selecting said sharpened element from a group consisting of a stylet or a needle.

It is another object of the present invention to provide the method as defined above, additionally comprising step of coupling said proximal portion of said fixating means (200) to appendages on said deployment means (3).

It is another object of the present invention to provide the method as defined above, additionally comprising step of coupling said proximal portion (200*a*) of said fixating means (200) to various locations on said deployment means (3), thus accommodating a variety of mesh sizes.

It is another object of the present invention to provide the method as defined above, additionally comprising step of extracting said deployment means from said abdominal cavity, and/or pre-peritoneal and/or hollow body organs and/or natural and/or artificial orifices and/or spaces and/or post operative spaces.

It is another object of the present invention to provide the method as defined above, additionally comprising step of deflating or minimizing said deployment means.

It is another object of the present invention to provide the method as defined above, additionally comprising step of continuing inflating or preserving the shape of said deployment means according to a predetermined medical need.

It is another object of the present invention to provide the method as defined above, additionally comprising step of fitting the center of said deployment means to the center of said hernia.

It is another object of the present invention to provide the method as defined above, additionally comprising step of threading centering means (5) through said mesh.

It is another object of the present invention to provide the method as defined above, ad comprising step of ensuring the right side of said mesh is directed to said hernia.

It is another object of the present invention to provide the method as defined above, additionally comprising step of ensuring the right direction of said mesh in the abdominal cavity.

It is another object of the present invention to provide the method as defined above, additionally comprising step of selecting the shape of said deployment means from a group comprising a polygonal shape, a curved shape, a symmetrical, a nor-symmetrical shape, a linear shape, continues, non-continues, a concave shape, a irregular shape, a square-like shape, a rectangular shape, an oval shape, a U-like shape, an H-like shape, a grid-like shape, a flat structure, a 3D structure and a rake-like shape or any combination thereof.

It is another object of the present invention to provide a method for attaching a mesh to deployment means, comprising steps selected inter alia from:

a. obtaining a hernia kit comprising:

i. a mesh (2);

ii. at least one deployment means (3), adapted to deploy said mesh with in the abdominal cavity and/or pre-peritoneal and/or hollow body organs and/or natural and/or artificial orifices and/or spaces and/or post operative spaces; and, iii. fixating means (200) coupled to said deployment means (3), adapted to attach said deployment means (3) to said mesh (2),

7 said fixating means are characterized by at least two portions:

a. a first portion (200*a*) coupled to said deployment means (3);

b. a second portion (200*b*), comprising a coil (252) having a predetermined retracted shape; said coil is reconfigurable from a plurality of unretracted positions to a plurality of retracted positions and from said plurality of retracted positions to said plurality of unretracted positions;

b. obtaining attaching means adapted to thread said second portion (200*b*) through said mesh (2);

c. reversibly coupling said attaching means to said second portion (200*b*);

d. threading said second portion (200*b*) through said mesh (2) via said attaching means;

e. reconfiguring said coil (252) from said retracted position to an unretracted position; thereby at least partially passing said coil through said mesh; and, f. reconfiguring said coil (252) from said unretracted position to said retracted position thereby attaching said mesh to said deployment means.

It is another object of the present invention to provide the method as defined above, additionally comprising step of selecting said deployment means from a group consisting of inflatable balloon.

It is another object of the present invention to provide the method as defined above, additionally comprising step of uncoupling said attaching means from said second portion (200*b*).

It is another object of the present invention to provide the method as defined above, additionally comprising steps of (a) adjusting said mesh attached to said deployment means; and, (b) inserting said adjusted deployment means attached to said mesh into the abdominal cavity and/or pre-peritoneal and/or hollow body organs and/or natural and/or artificial orifices and/or spaces and/or post operative spaces.

It is another object of the present invention to provide the method as defined above, additionally comprising step of spreading and/or deploying said mesh.

It is another object of the present invention to provide the method as defined above, wherein said step of spreading and/or deploying said mesh additionally comprising step of inflating or actuating said deployment means.

It is another object of the present invention to provide the method as defined above, additionally comprising step of coupling said fixating means (200) to said deployment means (3) by means selected from a group consisting of glue, Velcro, mechanical connections selected from a group consisting of a disc or a knot), welding means, threading or any combination thereof.

It is another object of the present invention to provide the method as defined above, wherein said step (e) of reconfiguring said coil from said retracted position to an unretracted position additionally comprising step of mechanically pulling said coil.

It is another object of the present invention to provide the method as defined above, wherein said step (f) of reconfiguring said coil unretracted position to said retracted position additionally comprising step of releasing said mechanical stress.

It is another object of the present invention to provide the method as defined above, wherein said step (e) or said step (f) of reconfiguring said coil is performed by means selected from a group consisting of application of electrical current on said coil, thermoregulating said coil, application of magnetic field on said coil.

It is another object of the present invention to provide the method as defined above, wherein said step (f) of reconfiguring said coil unretracted position to said retracted position is performed spontaneously.

It is another object of the present invention to provide the method as defined above, wherein said step of step (c) of reconfiguring said coil from said retracted position to an unretracted position additionally comprising step of transforming said coil to a more linear configuration.

It is another object of the present invention to provide the method as defined above, wherein said step (f) of reconfiguring said coil unretracted position to said retracted position additionally comprising step of transforming said coil to at least partially a helical and/or spiral configuration.

It is another object of the present invention to provide the method as defined above, additionally comprising step of selecting said coil to have more than one coiling radius.

It is another object of the present invention to provide the method as defined above, additionally comprising step of selecting said attaching means from sharpened element selected from a group consisting of a stylet or a needle.

It is another object of the present invention to provide the method as defined above, additionally comprising step of coupling said first portion of said fixating means (200) to appendages on said deployment means (3).

It is another object of the present invention to provide the method as defined above, additionally comprising step of coupling said first portion (200*a*) of said fixating means (200) to various locations on said deployment means (3), thus accommodating a variety of mesh sizes.

It is another object of the present invention to provide the method as defined above, additionally comprising step of extracting said deployment means from said hernia.

It is another object of the present invention to provide the method as defined above, additionally comprising step of deflating or minimizing said deployment means.

It is another object of the present invention to provide the method as defined above, additionally comprising step of continuing inflating or preserving the shape of said deployment means according to a predetermined medical need.

It is another object of the present invention to provide the method as defined above, additionally comprising step of fitting the center of said deployment means to the center of said hernia.

It is another object of the present invention to provide the method as defined above, additionally comprising step of threading centering means (5) through said mesh.

It is another object of the present invention to provide the method as defined above, additionally comprising step of ensuring the tight side of said mesh is directed to said hernia.

It is another object of the present invention to provide the method as defined above, additionally comprising step of ensuring the right direction of said mesh in the abdominal cavity.

It is another object of the present invention to provide the method as defined above, additionally comprising step of selecting the shape of said deployment means from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, an H-like shape, a grid-like shape, a flat structure, a 3D structure and a rake-like shape or any combination thereof.

It is another object of the present invention to provide s fixating means (200) adapted for use in hernia repair surgeries in attaching a mesh (2) and mesh deployment means (3); said fixating means are attached to said mesh deployment means (3); said fixating means (200) comprising:

a. a first portion (200a) coupled to said deployment means (3); and, b. a second portion (200b), comprising a coil (252) having a predetermined retracted shape; said coil is reconfigurable from a plurality of unretracted positions to a plurality of retracted positions and from said plurality of retracted positions to said plurality of unretracted positions;

wherein said attachment between said deployment means (3) and said mesh (2) is obtained by reconfiguration of said coil (252) from at least one of said unretracted positions to at least one of said retracted positions.

It is another object of the present invention to provide the fixating means as defined above, wherein said deployment means (3) is an inflatable balloon.

It is another object of the present invention to provide the fixating means as defined above, wherein said fixating means additionally comprising means reversibly coupled to said second portion, adapted to thread said second portion (200b) through said mesh (2).

It is another object of the present invention to provide the fixating means as defined above, wherein said fixating means additionally comprising a third portion (200c) having at least one sharpened element (256), adapted to fully penetrate said mesh (2).

It is another object of the present invention to provide the fixating means as defined above, wherein said retracted position is at least partially helical and/or spiral configuration.

It is another object of the present invention to provide the fixating means as defined above, wherein said fixating means (200) are coupled to said deployment means (3) by means selected from a group consisting of glue, Velcro, mechanical connections selected from a group consisting of a disc or a knot, welding means, threading means or any combination thereof.

It is another object of the present invention to provide the fixating means as defined above, wherein said unretracted position is at least partially linear configuration.

It is another object of the present invention to provide the fixating means as defined above, wherein said coil is made of materials selected from a group consisting of nylon, shape memory materials, Thermoplastic materials, Polyurethane, EAP, biodegradable materials or any combination thereof.

It is another object of the present invention to provide the fixating means as defined above, wherein said deployment means (3) is made of materials selected from a group consisting of nylon, shape memory materials, Thermoplastic materials, Polyurethane, EAP, biodegradable materials, stainless steel, other metals, plastic or any combination thereof.

It is another object of the present invention to provide the fixating means as defined above, wherein said coil is a coaxial structure, comprising an outer cannula with a longitudinal slit and an inner thread, such that said cannula collapses into a helical configuration after said inner thread is pulled out.

It is another object of the present invention to provide the fixating means as defined above, wherein said coil is reconfigurable from a retracted position to an unretracted position by means selected from a group consisting of mechanically pulling or pushing said coil, applying electrical current on said coil, thermoregulating said coil, applying magnetic field.

It is another object of the present invention to provide the fixating means as defined above, wherein said coil is spontaneously reconfigurable from a retracted position to an unretracted position.

It is another object of the present invention to provide the fixating means as defined above, wherein said coil has at least one coiling radius.

It is another object of the present invention to provide the fixating means as defined above, wherein said sharpened element is selected from a group consisting of a stylet or a needle.

It is another object of the present invention to provide the fixating means as defined above, wherein said deployment means (3) additionally comprising at least one appendage to which said first portion of said fixating means (200) is coupled.

It is another object of the present invention to provide the fixating means as defined above, wherein said first portion (200a) of said fixating means (200) is coupled to various locations on said deployment means (3), thus accommodating a variety of mesh sizes.

It is another object of the present invention to provide the fixating means as defined above, wherein said deployment means (3) is in communication with inflating means adapted to inflate said deployment means (3).

It is another object of the present invention to provide the fixating means as defined above, wherein the shape of said deployment means is selected from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, an H-like shape, a grid-like shape, a flat structure, a 3D structure and a rake-like shape or any combination thereof.

It is another object of the present invention to provide the fixating means as defined above, wherein said deployment means additionally comprising centering means adapted to adjust the center of said deployment means and said mesh to the center of said hernia.

It is another object of the present invention to provide the fixating means as defined above, wherein said deployment means additionally comprising means adapted to ensure the right side of said mesh is directed to said hernia.

It is another object of the present invention to provide the fixating means as defined above, wherein said deployment means additionally comprising means adapted to ensure the right direction of said mesh in the abdominal cavity.

It is another object of the present invention to provide the fixating means as defined above, wherein said centering means additionally comprising means adapted to thread said centering means through said mesh.

It is still an object of the present invention to provide the fixating means as defined above, wherein said deployment means additionally comprising at least one clip adapted to grab sutures.

It is lastly an object of the present invention to provide the fixating means as defined above, wherein said centering means additionally comprising means (9) adapted to enable the grasp of said centering means with a surgical tool.

BRIEF DESCRIPTION OF THE DRAWINGS

FIGS. 5A-5L schematically represent other embodiments of the coil part of the fixating means.

FIGS. 9A-9B discloses a method for using the preferred embodiment of the fixating means.

FIGS. 10A, 10B, and 11 illustrate another embodiment of the present invention.

DETAIL DESCRIPTION OF THE SPECIFIC EMBODIMENTS

Figure 1A:
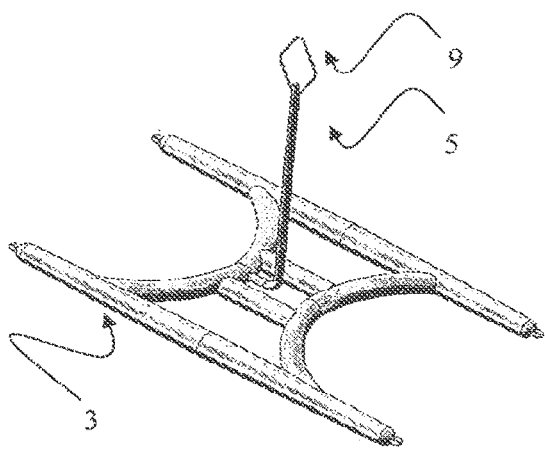
FIGS. 1A-1C schematically illustrate one embodiment of deployment means (e.g., inflatable balloon) and mesh for treating abdominal hernia.

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide a fixating means between a mesh and a mesh deployment means.

The term "coil" refers hereinafter to any flexible and elastic object (e.g., any wire or spring) that can store mechanical energy. Said coil has a predetermined retracted spatial shape and is adapted to restore said shape when mechanical loads, electrical forces, magnetic forces or any combination thereof loads are applied on said coil. Furthermore said coil is adapted to alter its spatial shape to an unretracted spatial shape when force (e.g., mechanical, magnetic, electrical, or any combination of forces thereof) is applied on it. Furthermore said coil is adapted to alter its spatial shape back to a retracted spatial shape when said force (e.g., mechanical, magnetic, electrical, or any combination of forces thereof) is applied on it again and/or removed. In a preferred embodiment said object comprises a long and narrow thread, twine, wire, cord, filament, fiber, floss or filum.

The term "balloon" refers hereinafter to any flexible bag which can inflates or expands. The balloon can be made from materials such as rubber, latex, silicone, polyurethane, chloroprene or a nylon fabric or any thermoelastomeric materials or any combination of materials thereof. The balloon can be made of biocompatible materials, self-dissolving materials or shape memory materials.

The term "deployment means" refers hereinafter to any device adapted to spread and/or position meshes in any body cavity. The mesh deployment means can be made of any rigid, stiff or flexible materials. It can be made of stainless steel, other metals, plastic, biocompatible materials, electro-active polymers, biodegradable materials, shape memory materials, nylon, thermoelastic or thermoplastic materials, or any combination of materials thereof. In a specific embodiment of the present invention, the deployment means are an inflatable balloon.

The term "side of the mesh" refers hereinafter to two sides of the mesh, one which faces the abdominal wall and the other faces the bowels.

The term "orientation or direction of the mesh" refers hereinafter to orientation of the mesh within the abdominal cavity, i.e., the ability to rotate the mesh within the abdominal cavity.

Usually the mesh is not symmetric in shape (i.e., rectangular or i.e., ellipse)—therefore it has different directions, By rotating the mesh within the abdominal cavity—one can decide what direction is turned where.

The term "Hernia" refers hereinafter to hernia in the abdominal cavity or in pre-peritoneal. Moreover the term hernia may be regarded as umbilical hernia, hiatal hernia, ventral hernia, postoperative hernia, epigastric hernia, spiegelian hernia, inguinal hernia and femoral hernia, generally any abdominal wall related hernia.

Yet more, it may be regarded in the most general interpretation as hernia in any hollow body organs and/or said natural and/or said artificial orifices and/or said spaces and/or said post operative spaces.

The terms "mesh" and/or "patch" refers hereinafter in a non-limiting manner to a flexible plane member of desired contour, selected in a non-limiting manner from biocompatible compositions selected from polymeric compositions; glassware; titanium containing, stainless still, nitinol (Nickel Titanium alloys), and or other metal ware; composite materials; cardboard, natural fiber, silicone, rubber or rubber-like compositions or any mixture thereof.

The term "minimally invasive surgery" refers hereinafter to a procedure that is carried out by entering the body through the skin or through a body cavity or anatomical opening, but with the smallest damage possible.

The term "trocar" refers hereinafter to a surgical instrument passed through the body or abdominal wall, used to allow easy exchange of endoscopic instruments during endoscopic or other minimally invasive surgery.

The term "Biocompatible materials" refers hereinafter to materials that have the ability to perform with an appropriate host response in a specific application. Biocompatible materials have the quality of not having toxic or injurious effects on biological systems.

The term "adjusting" refers hereinafter to rolling, bending, twisting, folding and winding of the mesh, thus preparing and enabling the insertion of said mesh into the body.

The term "biodegradable materials" refers hereinafter to materials that are degraded by the body's enzymatic and/or hydrolytic pathways through a reaction against "foreign" material. Some urologists may prefer self-dissolving materials in catheter simply because then they don't have to go necessarily through the procedure of removing them afterwards. Examples of self-dissolving polymers are Polydioxanone (PDO), Polycaprolactone (PCL), Polylactic acid (PLA), Polyglycolic acid (PGA), Adipic acid, PEG and glutamic acid.

The term "shape memory materials" refers hereinafter to materials which can "remember" there original geometry. After a sample of shape memory materials has been deformed from its original geometry, it regains its original geometry by itself during heating (one-way effect) or, at higher ambient temperatures, simply during unloading (pseudo-elasticity or superelasticity). The thermally induced shape-memory effect has been described for different material classes: polymers, such as polyurethanes, poly(styrene-block-butadiene), Polydioxanone and polynorbornene, metallic alloys, such as copper-zinc-aluminium-nickel, copper-aluminium-nickel, and nickel-titanium (NiTi) alloys.

The term "Electroactive Polymers or EAPs" refers herein after to polymers whose shape is modified when a voltage is applied to them. EAP can have several configurations, but are generally divided in two principal classes:

1. Dielectric EPAs, in which actuation is caused by electrostatic forces between two electrodes which squeeze the polymer. This kind of EAP is characterized by a large actuation voltage (several thousand volts). Examples are electrostrictive polymers and dielectric elastomers.

2. Ionic EAPs, in which actuation is caused by the displacement of ions inside the polymer. Only a few volts are needed for actuation. Examples of ionic EAPS are conductive polymers, ionic polymer-metal composites (IP-MCs), and responsive gels. The present invention provides a hernia kit useful in minimal invasive and/or open surgery. The hernia kit comprises:

a. a mesh (2);

b. at least one deployment means (3), adapted to deploy said mesh within the abdominal cavity and/or pre-peritoneal and/or hollow body organs and/or natural and/or artificial orifices and/or spaces and/or post operative spaces; and, c. fixating means (200) coupled to said deployment means (3), adapted to attach said deployment means (3) to said mesh (2); said fixating means are characterized by at least two portions:

i. a first (proximal) portion (200a) coupled to said inflatable deployment means (3);

ii. a second (middle) portion (200b), comprising a coil (252) having a predetermined retracted shape; said coil is reconfigurable from a plurality of unretracted positions to a plurality of retracted positions and from said plurality of retracted positions to said plurality of unretracted positions;

wherein said attachment between said deployment means (3) and said mesh (2) is obtained by reconfiguration of said coil (252) from at least one of said unretracted positions to at least one of said retracted positions.

The attachment is obtained by bringing into physical contact and holding together said mesh and said mesh deployment means.

It should emphasize that according to a preferred embodiment of the present invention, said deployment means (3) is an inflatable balloon. However, the present invention could be suitable to any deployment system.

It is another object of the present invention to provide the hernia kit as defined above, wherein said fixating means additionally comprising attaching means reversibly coupled to said second portion, adapted to thread said second portion (200b) through said mesh (2).

It should be emphasized that said attaching means could be any means that can insert the coil through the mesh.

According to one embodiment of the present invention the fixating means additionally comprises a third (distal) portion (200c) comprising at least one sharpened element (256), adapted to fully penetrate said mesh (2).

As discussed earlier, one of the time consuming procedures or obstacle is the attachment of the mesh (and/or the patch) to the deployment means.

The present invention provides means for said attachment by threading attachment means that are connected to the deployment means, into or through the mesh.

Figure 1B:
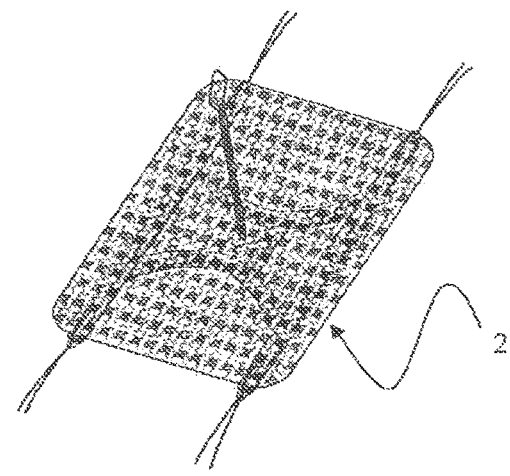

It should be emphasized that the following discloser describes an inflatable balloon as the deployment means. However, any other mesh/patch deployment means can be used as well. Reference is now made to FIGS. 1a and 1b which schematically displays in a non limiting manner one embodiment of a mesh deployment means (e.g., inflatable balloon) (3) and the mesh (2) in the hernia kit. The figures illustrate the inflatable balloon (3) that serves as the deployment mean according to one embodiment of the present invention with (FIG. 1b) and without (FIG. 1a) a mesh (2). The fixating means (200) are illustrated in the following figures.

The deployment means (3) can be made of materials selected from a group comprising of biocompatible materials, Nylon, self-dissolving materials, Thermoplastic Polyurethane, EAP and shape memory materials and any combination of materials thereof.

The shape of the deployment means (3) can be an eccentric shape a concentric shape, an "H"; modified "H", shape a polygonal shape, a curved shape, a symmetrical shape, a non-symmetrical shape, a linear shape, a branching shape, a continuous shape, a non-continuous, a concave shape, a irregular shape, a square-like shape, a U-like shape, a grid-like shape and a rake-like shape or any combination thereof.

If a balloon is used as the deployment means (3)—thus it can be inflated by air, CO2, saline etc. in order to inflate the balloon, inflating means are coupled to the balloon (not shown in the figures).

If the deployment means is not a balloon, it's shape can be modified and/or at least one of it's parts can be actuated to allow the spreading and/or deploying of the mesh. The deployment means (e.g., the inflating balloon) (3) may also comprise a centering means (5), for ensuring that the center of said deployment means (e.g., inflatable balloon) and thus the center of the mesh will be aligned with the center of said hernia.

Furthermore, said centering means enable to move said deployment means (e.g., the balloon) and thus the mesh into the desired position inside the abdominal cavity. The distal part of the centering means may be attached to grasping means (e.g., a needle or a closed loop) (9) enabling said movement of said deployment means (e.g., inflatable balloon) and the mesh. Said means (9) enables the grasp of said centering means (5) via a surgical tool.

Figure 1C:
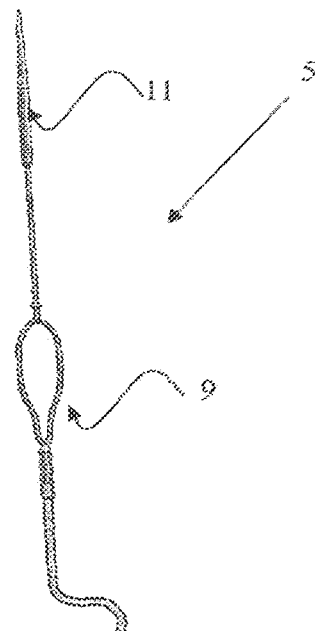

Reference is now made to FIG. 1c illustrating a closer view of another possible embodiment of said centering means (5). According to said embodiment, the centering means (5) comprises grasping means (9) which is a closed loop coupled to a needle/sharp element (11). Needle (11) is provided to enable with the penetration of said centering means (5) through the mesh.

Figure 2A:
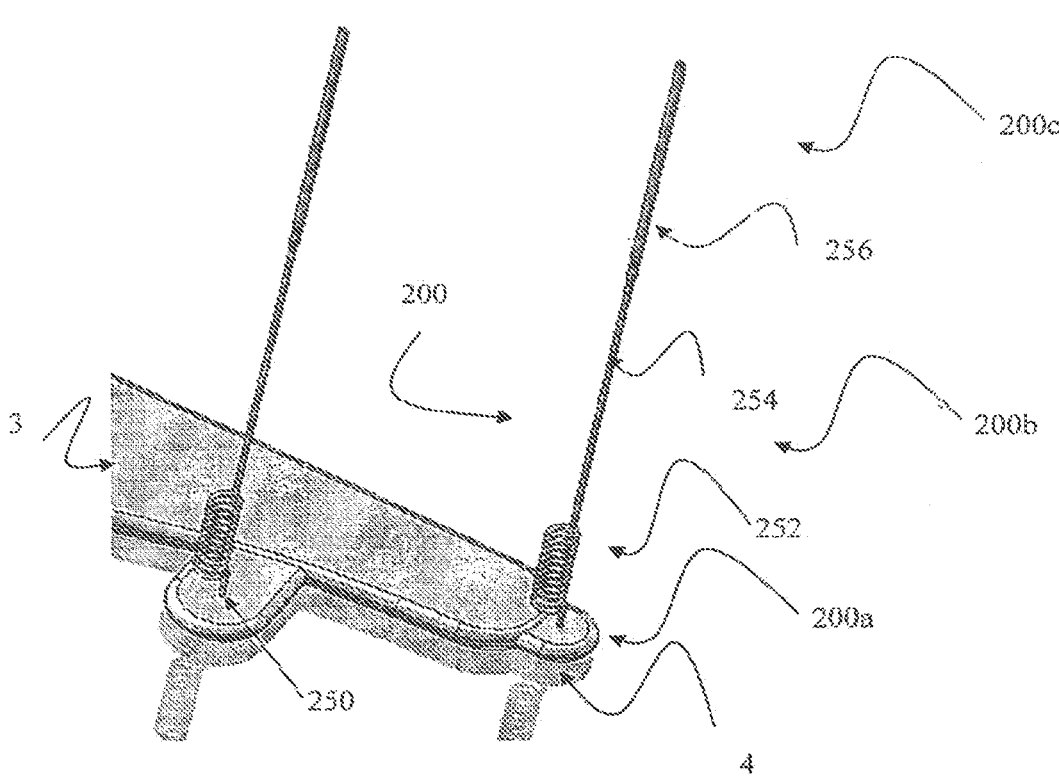
FIGS. 2A-2C schematically illustrates appendages of the deployment means (e.g., the inflatable balloon) and the preferred embodiment of a fixating means.

It should be emphasized that according to a preferred embodiment of the present invention, if the deployment means are an inflatable; balloon thus the centering means (5) are also the inflating means adapted to inflate or deflate the inflatable balloon (3). Reference is now made to FIG. 2a, schematically representing a preferred embodiment of the fixating (attachment) means (200) which are adapted to attach the mesh to the deployment means (e.g., the inflating balloon).

FIG. 2a also represents the appendages (4) of the deployment means (e.g., the inflatable balloon) (3).

The distal portion (200e) of the fixating means (200) comprises a stylet (256) or any other sharp object (e.g., needle), which can puncture the deployment means' (e.g., the inflating balloon's) appendage (4) and the mesh.

According to another embodiment, the deployment means (e.g., the inflating balloon) will have appendages having at least one aperture through out which the stylet (256) passes. Thus, the stylet (256) only have to puncture the mesh.

The proximal portion (200a) of the fixating means (200) is coupled to the deployment means (e.g., the inflatable balloon) (3). The coupling of the proximal portion and the deployment means (e.g., the inflatable balloon) could be obtained by glue, Velcro mechanical connections (such as for example a disc or for example a knot), or by welding or threading of the proximal portion (200a) to the appendages (4) or to any other part of the deployment means, or any combination thereof.

The middle portion (200b) of the fixating means (200) is a suture cord or an injected material or a pre formed material which comprises according to one embodiment two sections.

The first section (252) serves as a self retracting coil (e.g., helical), which can be actively pulled into a more elongated and less unretracted configuration (said part will refer hereinafter as the helical part or the coil (252)).

The second section (254) is a relatively linear part of the fixating means (200) which connects the helical part to the sharpened part, it should be emphasized that this second section can be removed after the sharpened end is inserted through the mesh.

According to another embodiment, the middle portion (200b) of the fixating means (200) is a suture cord or an injected or a pre formed material which comprises only the first section (252)—i.e., the self retracting coil.

FIG. 2a also represents the appendages (4) of the deployment means (e.g., the inflatable balloon) (3). The appendages (4) can be made of the same material as the inflatable balloon (3), being a direct extension of the inflatable balloon (3). It can also be made of another material coupled or attached to the deployment means (e.g., the inflatable balloon) (3).

Figures 2B, 2C:
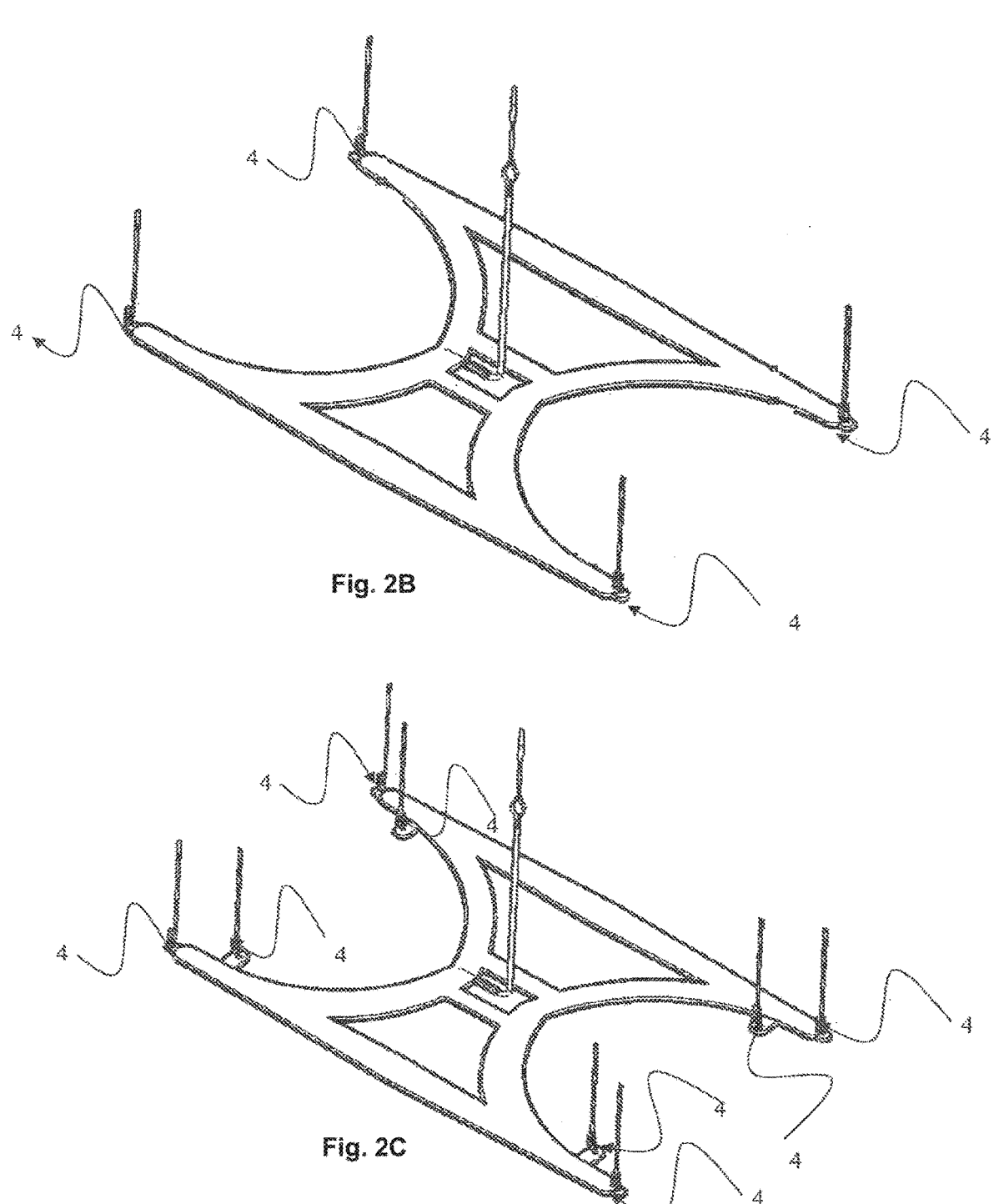

It should be emphasized that the deployment means (e.g., the inflatable balloon) (3) may have a different number of appendages (4), it could be for example 4 (as demonstrated in FIG. 2b) or for example 8 (as demonstrated in FIG. 2c).

According to one embodiment of the present invention, the fixating means (200) can be made of any flexible or rigid materials. According to another embodiment the fixating means (200) can be made of nylon, biodegradable material, EAP, shape memory materials, Thermoplastic Polyurethane or any combination thereof.

Reference is now made to FIGS. 3a-3e, schematically representing a method of fixating the mesh (2) to the deployment means (e.g., the inflatable balloon) (3) using the preferred embodiment of a fixating means shown in FIG. 2).

Figure 3A:
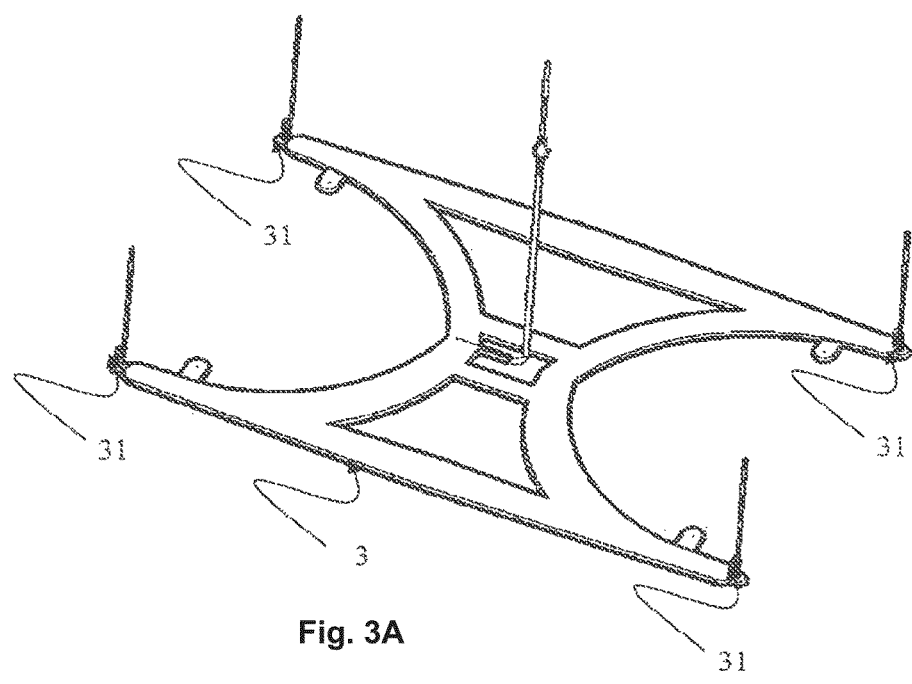
FIGS. 3A-3F schematically represent a method of fixating the mesh to the deployment means (e.g., the inflatable balloon) using the preferred embodiment of a fixating means.

At the initial configuration, the fixating means (200) are attached to the deployment means (e.g., the inflatable balloon) (3) at diverse locations (denotes as numerical reference (31)), chosen to optimize the covering of the deployment means (e.g., the inflatable balloon) (3) by the mesh (2) (FIG. 3a).

Next, the stylet (256) of each fixating means (200) is pulled through the mesh at the appropriate locations.

It should be pointed out that if the fixating means (200) are not connected to the deployment means (e.g., the balloon), then the stylet (256) is threaded through the appendages (4) or through insertion holes (250) in the appendages (4) and then into the mesh (2).

Figure 3B:
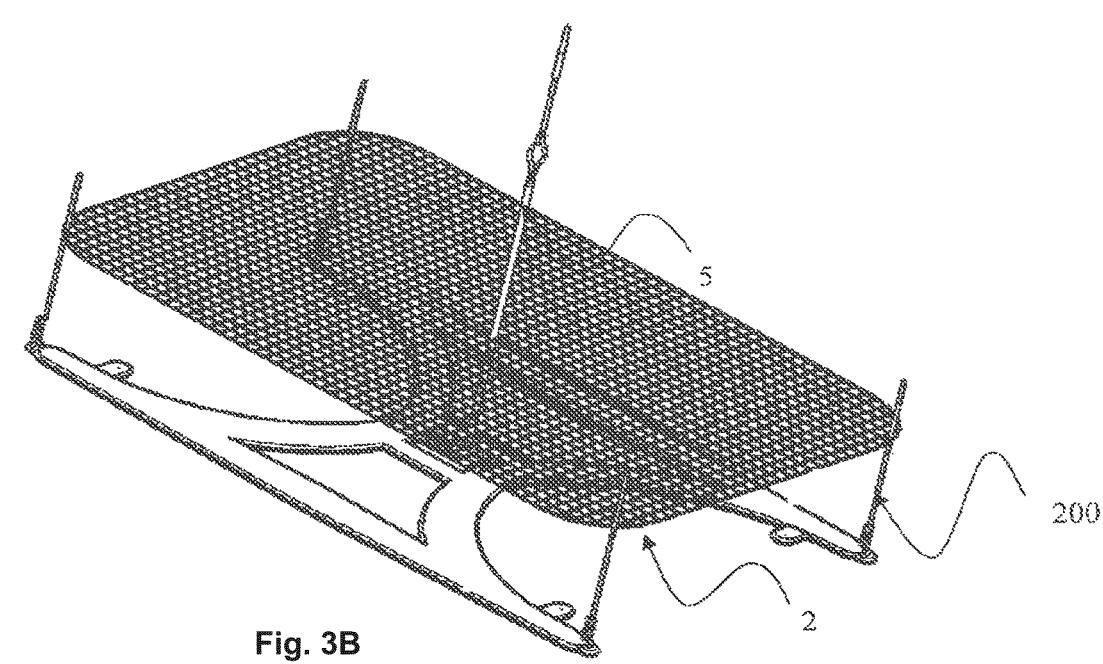

It should be noted that if centering means (5) exists, it can also be pulled through the mesh FIG. 3b).

Next, the retracted part (i.e., coil (252)) of fixating means (200) is pulled into a less retracted configuration (FIG. 3c) and passes through the mesh. In other words, the configuration of the coil (252) is altered from a retracted position (e.g., helical shape) into an unretracted position (e.g., at least partially linear shape).

Figure 3C:
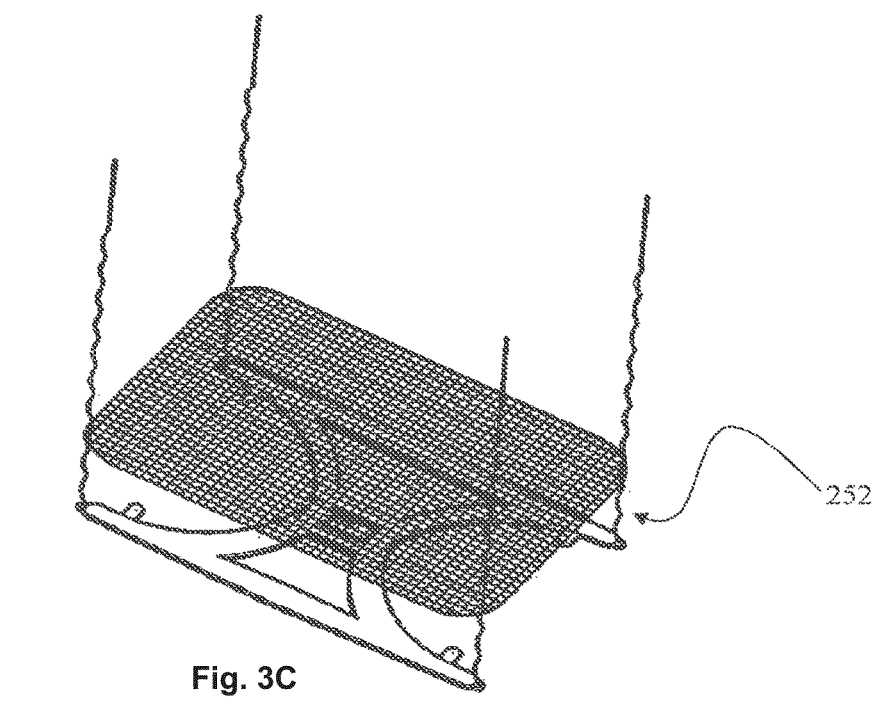
Figure 3D:
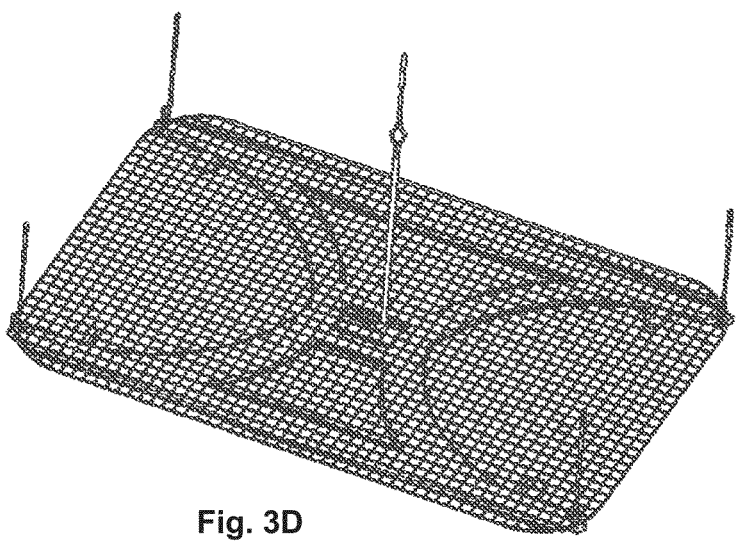
Figure 3E:
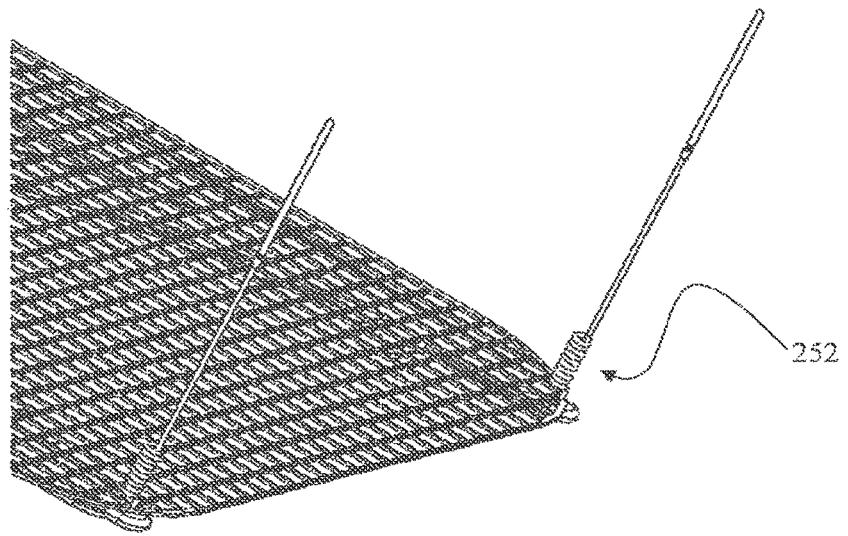

As it is released (i.e., the mechanical stress is released), it resumes its retractable position, pushing and driving the mesh against the deployment means (e.g., the inflatable balloon) (3) (FIGS. 3d and 3c). In other words, the configuration of the coil (252) is retracted from said unretracted position (e.g., at least partially linear shape) into a retracted position (e.g., helical shape).

Other retraction options may be either due to intrinsic elastic or magnetic properties of the coil (252) of fixating means (200), or by an external stimulation, such as applying electric current (in case of EAP), applying heat (in case of a shape memory material), applying mechanical means or any other means of actuating a helical configuration.

According to another embodiment of the present invention, the coil (252) is a coaxial structure, comprising at least partially, helical and/or spiral structure that can unretract to a more linear structure, and retract back to at least partially, helical and/or spiral structure.

According to another embodiment of the present invention, the coil (252) is a coaxial structure, comprising an outer cannula with a longitudinal slit and an inner thread. The retraction of said coil is performed pulling out the inner thread thus the cannula collapse into a helical configuration.

It should be emphasized that the attachment between the mesh and the deployment means (e.g., the inflatable balloon) is most preferably done as preparation prior to the abdominal insertion, but it could also be used during a laparoscopic operation.

Figure 3F:
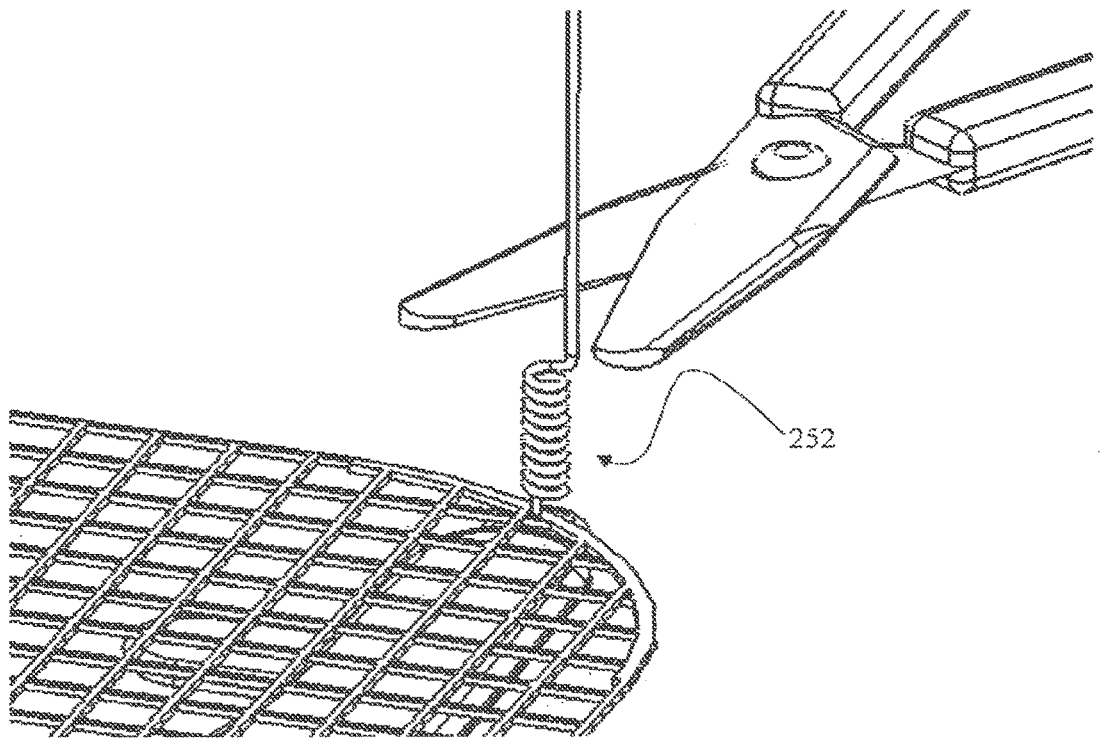

The linear part (254) of the fixating means (200) and/or the stylet (256) are then may be cut away (FIG. 3f), and the mesh is fixated to the deployment means (e.g., the inflatable balloon) (3).

The flexible part of fixating means (254) can alternatively be ablated by an electrical current, when the stimulation for coil retraction is an electrical current.

Alternatively only the stylet (256) is then may be cut away.

Figure 4A:
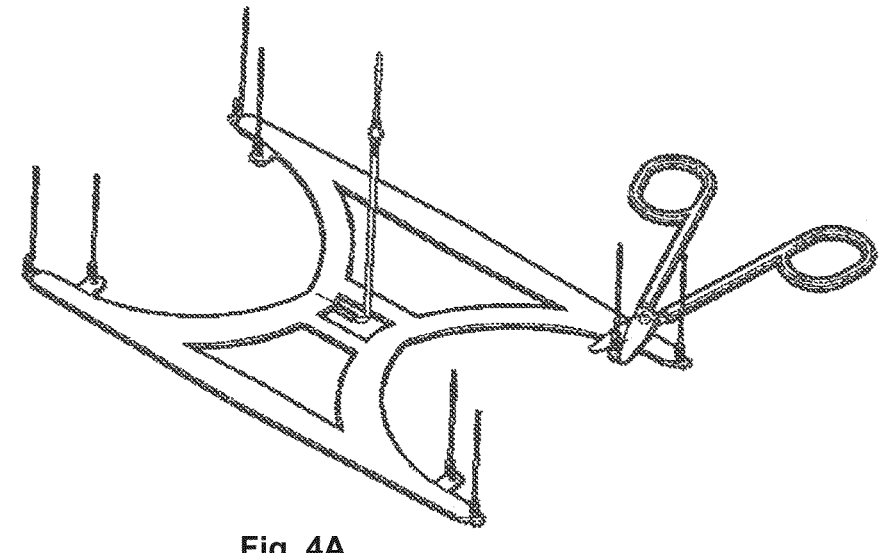
FIGS. 4A-4B schematically represent the adjustment of the preferred embodiment of a fixating means to different size of a mesh.
Figure 4B:
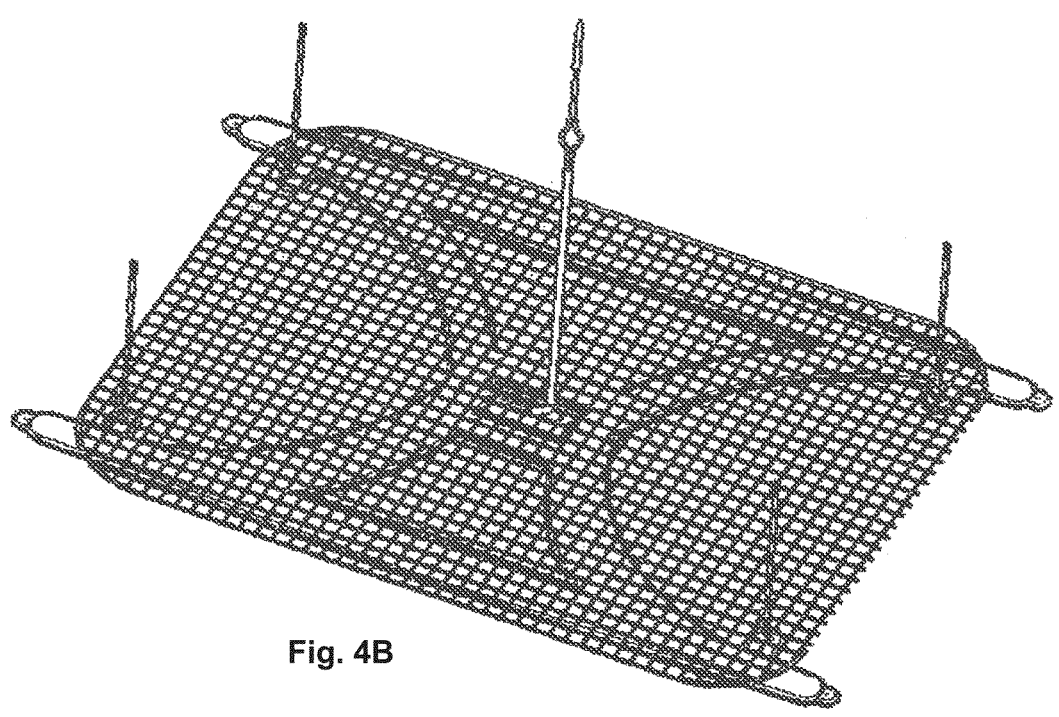

FIGS. 4a to 4b schematically represent the adjustment of the preferred embodiment of a fixating means to different size of a mesh. The appendages (4) and the fixating means (200) can be located at various locations (FIG. 4a), thus enabling the use of a mesh smaller than the deployment means (e.g., the inflatable balloon) (3) size (FIG. 4b).

Figure 5A:
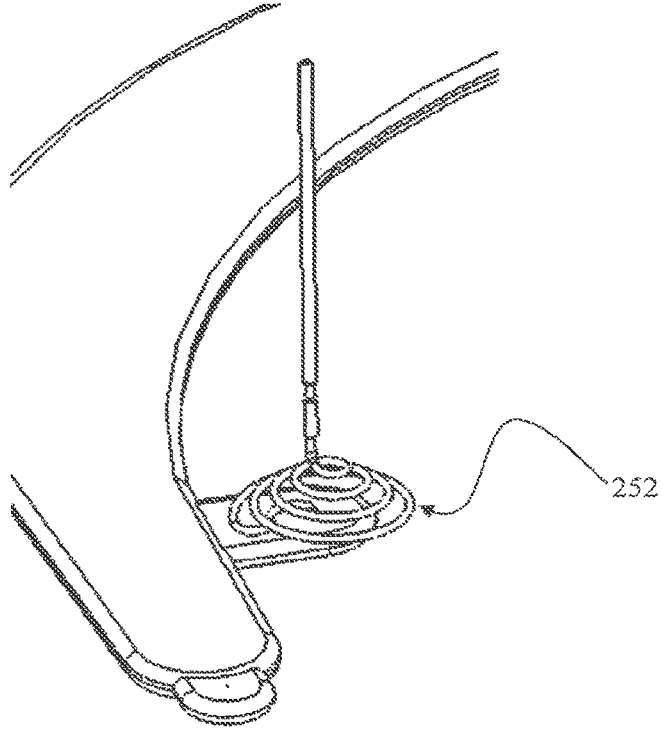

FIGS. 5a to 5b schematically represent other embodiments of the helical part (252) of the fixating means (200), which can have a varying radius of coiling (FIG. 5a) and varying number of rotations (FIG. 5b).

Reference is now made to FIGS. 5e-5f shows another preferred embodiment of the fixating (attachment) means (200). According to that embodiment all parts of the fixating means (252, 254 and 256) lay in the same plane.

FIG. 5c illustrates the fixating (attachment) means (200) having anchoring means (201). Said anchoring means can be encapsulated within the appendages (4) or trapped below the appendages (4).

FIG. 5d illustrate the fixating (attachment) means (200) displayed in FIG. 5c encapsulated within the appendages (4).

FIG. 5e illustrates another embodiment of the fixating (attachment) means (200) having different shape to the anchoring means (201).

FIG. 5f illustrate the fixating (attachment) means (200) displayed in FIG. 5e encapsulated within the appendages (4).

FIG. 5g illustrates another embodiment of the fixating (attachment) means (200) having different shape to the anchoring means (201).

FIG. 5h illustrate the fixating (attachment) means (200) displayed in FIG. 5g encapsulated within the appendages (4).

FIG. 5i illustrates another embodiment of the fixating (attachment) means (200) having different shape to the anchoring means (201).

FIGS. 5j-5k illustrate the different anchoring means (201) displayed in FIG. 5i trapped below the appendages (4).

FIG. 5l illustrate the different anchoring means (201) displayed in FIG. 5i encapsulated within the appendages (4).

It should be emphasized that the anchoring of the anchoring means can be reinforced with glue, welding, magnetic forces or any combination thereof.

Figures 6A, 6B, 6C, 6D, 6E, 6F, 6G, 6H:
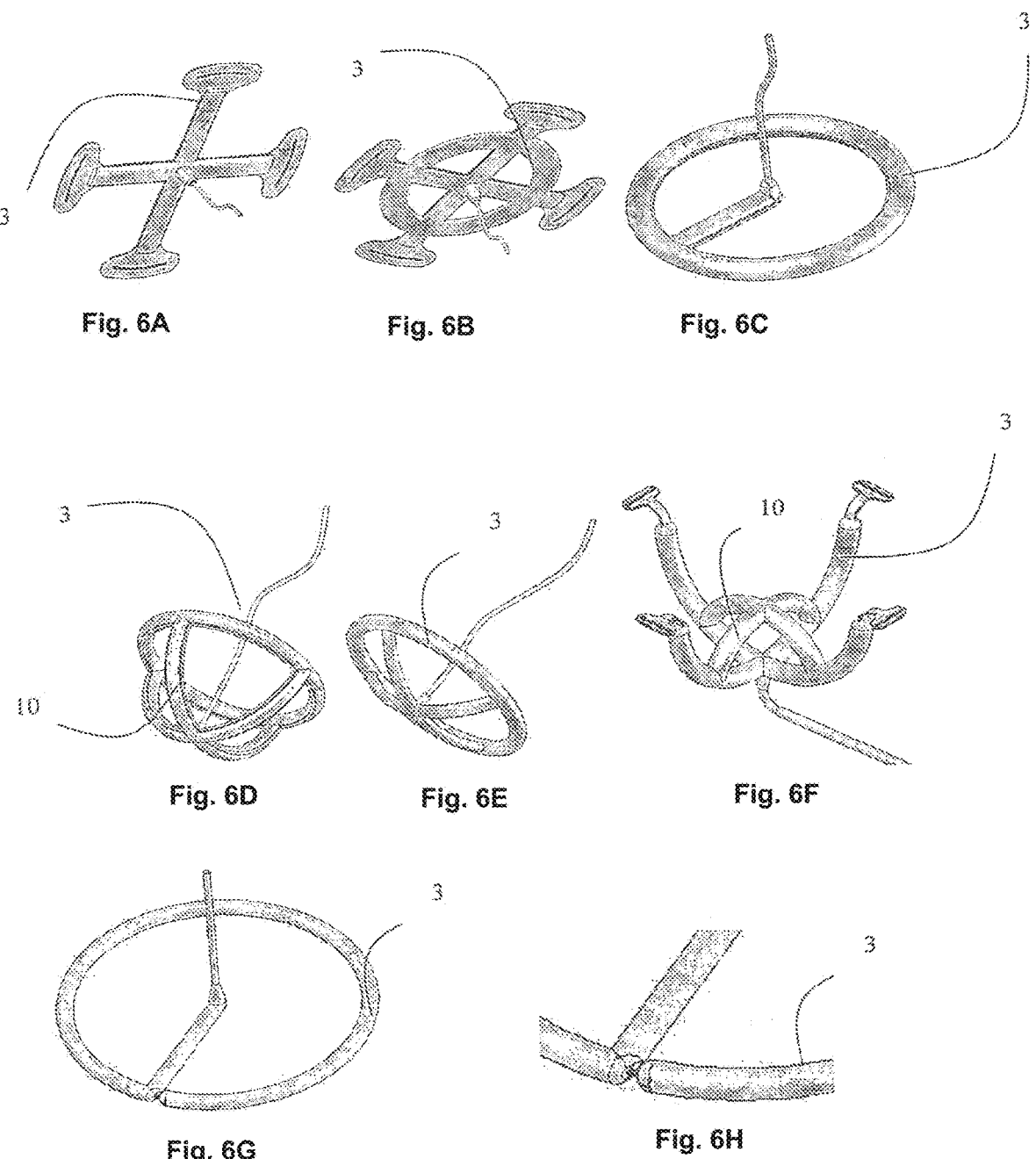
FIGS. 6A, 6B and 6C are a schematic drawing of the deployment means (e.g., the inflatable balloon) having a flat structure.
FIGS. 6D, 6E and 6F are a schematic drawing of the deployment means (e.g., the inflatable balloon) having a 3D structure.
FIGS. 6G and 6H are a schematic drawing of the deployment means (e.g., the inflatable balloon) with an incomplete structure.

The following figures are examples of different inflating balloons used as deployment means:

The inflatable balloon (3) may have a flat structure as displays in FIGS. 6a, 6b and 6c, or a 3D structure as displays in FIGS. 6d, 6e and 6f.

FIGS. 6d and 6f illustrate a 3D structure of the balloon which additionally comprises at least two arcs 10. The inflated balloon 3 is fixed to place by creating pressure on the mesh/patch towards the abdominal wall The inflatable balloon (3) may not have a complete closed shape as can be seen in FIGS. 6g and 6h. The parts of the balloon may be connected to each other with glue, wire, scotch Etc. As described above, if an inflating balloon is used as deployment means, thus the balloon will be coupled to an inflating means adapted to inflate said balloon.

When the deployment means (e.g., the inflatable balloon) is used in hernia repair surgeries it can additionally comprise means (such as bulge, lines, signs and symbols) for adjusting the center of said deployment means (e.g., the inflatable balloon) to the center of said hernia. Moreover the deployment means (e.g., the inflatable balloon) may additionally comprise means (such as bulge, lines, signs and symbols), adapted to ensure that the right side of the mesh (or patch) is directed to the abdominal or the pre-peritoneal cavity. Moreover the deployment means (e.g., the inflatable balloon) may additionally comprise means (such as bulge, lines, signs and symbols), adapted to ensure the right direction of the mesh in the abdominal cavity.

Figure 7:
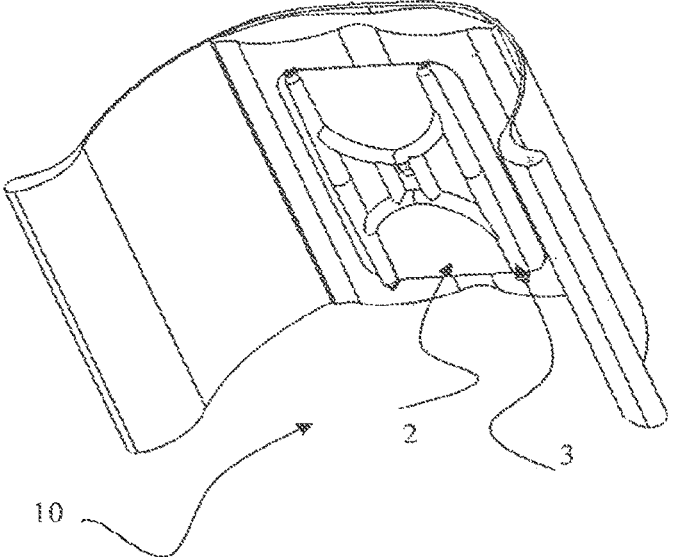
FIG. 7 schematically represents one embodiment of an inflatable balloon as a deployment means inside the abdominal cavity.

Reference is now made to FIG. 7 which schematically represents one embodiment of an inflatable balloon (3) used as deployment means and the mesh (2) inside the abdominal cavity 10.

Figure 8A:
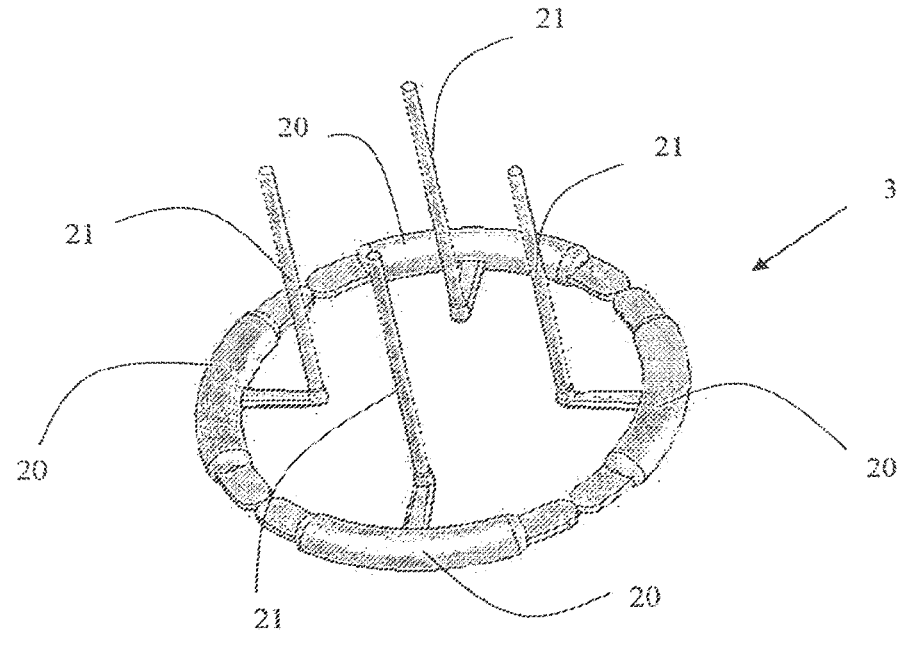
FIGS. 8A-8B schematically represent the inflatable balloon as the deployment means comprising several independent parts.
Figure 8B:
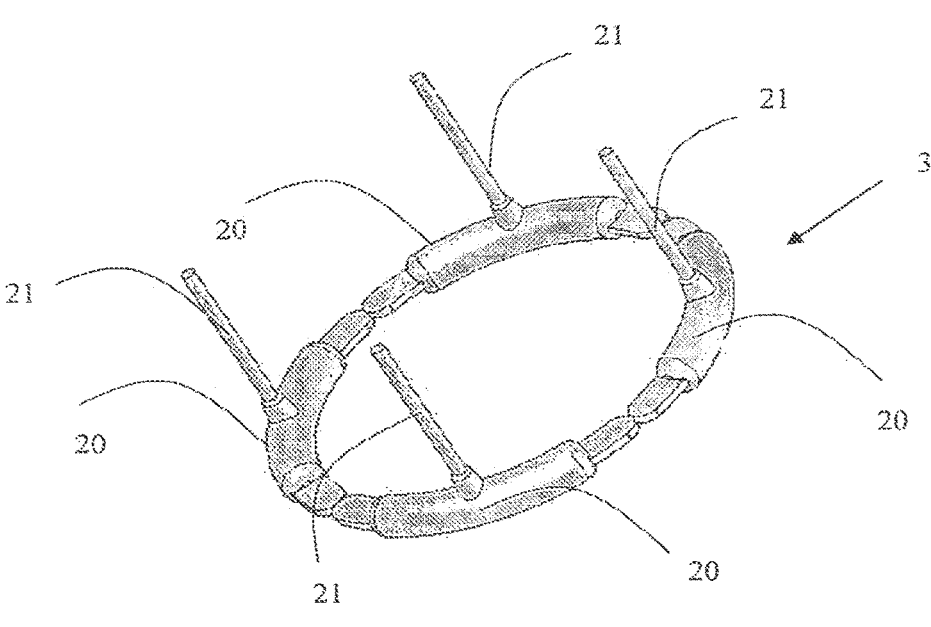

It should be emphasized that the inflatable balloon might be composed of several parts. Each of said par (will be coupled to an inflating means. Reference is now made to FIGS. 8a, 8b which schematically display an inflatable balloon having several independent parts 20 and several inflating tubes 21 (which will lately be couple to the inflating means). In the same manner other deployment means may comprise of several independent parts and several independent connectors and other mechanical park enabling the deployment of meshes/patches.

According to another embodiment of the present invention the deployment means (e.g., inflatable balloon) additionally comprising means adapted to adjust the center of said deployment means (e.g., the inflatable balloon) to the center of said hernia.

According to another embodiment of the present invention the deployment means (e.g., the inflatable balloon) additionally comprising means (11) adapted to thread said centering means through the mesh and/or through the abdominal wall (9) (as can be seen in FIG. 1c).

According to another embodiment of the present invention the deployment means (e.g., the inflatable balloon) additionally comprising means adapted to ensure the right side of said mesh is directed to the hernia.

According to another embodiment of the present invention the deployment means (e.g., the inflatable balloon) additionally comprising means adapted to ensure the right direction of the mesh in the abdominal cavity.

Figure 9A:
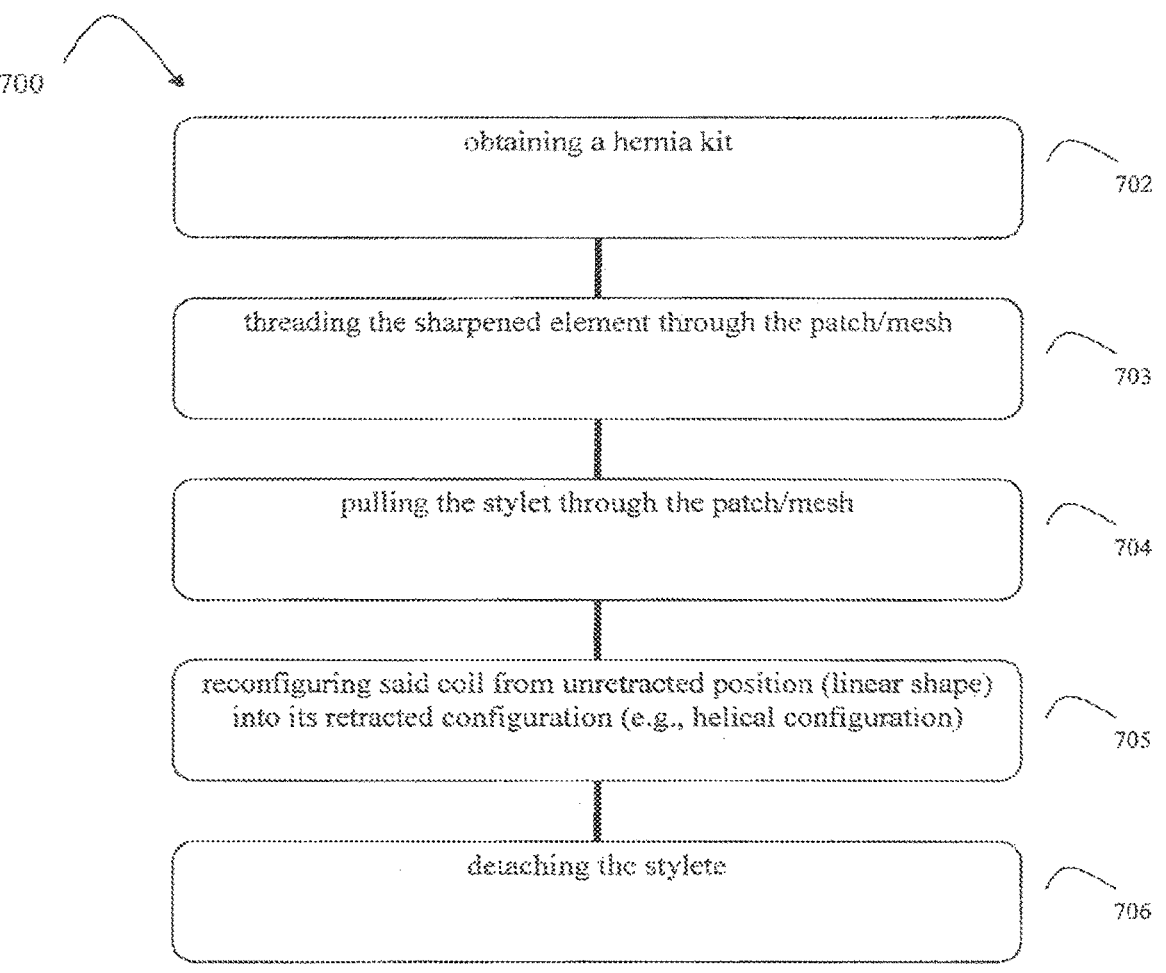

FIG. 9a illustrates in a flowchart for a method (700) for attaching a mesh to deployment means according to the preferred embodiment of the fixating means. The method comprises steps of obtaining (step 702) a hernia kit comprising:
- i. a mesh (2);
- ii. at least one deployment means (3), adapted to deploy said mesh with in the abdominal cavity and/or pre-peritoneal and/or hollow body organs and/or natural and/or artificial orifices and/or spaces and/or post operative spaces; and,
- iii. fixating means (200) coupled to said deployment means (3) adapted to attach said deployment means (3) to said mesh (2); said fixating means are characterized by:
  - a. a first (proximal) portion (200a) coupled to said deployment means (3);
  - b. a second (middle) portion (200b), comprising a coil (252) having a predetermined retracted shape; said coil is reconfigurable from a plurality of unretracted positions to a plurality of retracted positions and from said plurality of retracted positions to said plurality of unretracted positions; and,
  - c. a third (distal) portion (200c) comprising at least one sharpened element (256), adapted to fully penetrate said mesh (2);

The next step is to thread the sharpened element (i.e., stylete 256) through the mesh (2) (step 703).

Then, the stylet (256) is pulled through the mesh (2) (step 704) thus, reconfiguring the coil (252) from a retracted (e.g., helical) configuration into at least partially linear configuration.

Next (step 705), re-actuating the coil (252) of the fixating means (200) thus, reconfiguring said coil (252) from unretracted position (linear shape) into its retracted configuration (e.g., helical configuration).

Then (step 706) the sharpened element (i.e., stylete 256) is detached.

It should be emphasized that it is optionally to detach the also the linear part (254) of fixating means (200) from the coil (252).

Once the sharpened element is removed, the mesh (which is attached to the deployment means) is adjusted and inserted into the abdominal cavity and/or pre-peritoneal and/or hollow body organs and/or natural and/or artificial orifices and/or spaces and/or post operative spaces.

According to one embodiment of the present invention the deployment means are an inflated balloon (3). However, it should be emphasized that the above mentioned method can be employed on any deployment means and it should not be restricted to an inflatable balloon. According to another embodiment of the present invention, the method as described above additionally comprising step of uncoupling said attaching means from said second portion (200b).

According to another embodiment of the present invention, the retracted shape of the coil (252) is at least partially helical and/or spiral.

According to another embodiment of the present invention, the method as described above additionally comprising step of adjusting said mesh attached to said deployment means and inserting said adjusted deployment means attached to said mesh into the abdominal cavity and/or pre-peritoneal and/or hollow body organs and/or natural and/or artificial orifices and/or spaces and/or post operative spaces.

According to another embodiment of the present invention, the method additionally comprising step of inflating at least a portion of said inflatable balloon or actuating at least one part of other deployment means; thereby spreading and/or deploying said mesh.

According to another embodiment of the present invention, the method additionally comprising step of coupling said fixating means (200) to said deployment means (e.g., the inflatable balloon) (3) by means selected from a group consisting of glue, Velcro mechanical connections (such as fir example a disc or for example a knot), welding of the proximal portion (200a) to the appendages (4), threading said fixating means through the appendages (4) or through holes in the appendages (4) or through any other part of the deployment means or any combination thereof.

According to another embodiment of the present invention, the step of reconfiguring said coil from said retracted position to an unretracted position additionally comprising step of mechanically pulling said coil.

According to another embodiment of the present invention, the step of reconfiguring said coil from said unretracted position to said retracted position additionally comprising step of releasing said mechanical stress.

According to another embodiment of the present invention, the step of reconfiguring said coil is performed by means selected from a group consisting of application of electrical current on said coil, thermoregulating said coil, application of magnetic field on said coil or any combination of means thereof.

According to another embodiment of the present invention, the step of reconfiguring said coil from said unretracted position to said retracted position is performed spontaneously.

According to another embodiment of the present invention, the method additionally comprising step of selecting said coil to have more than one coiling radius.

According to another embodiment of the present invention, the method additionally comprising step of selecting said sharpened element from a group consisting of a stylet or a needle.

According to another embodiment of the present invention, the method additionally comprising step of coupling said proximal portion of said fixating means (200) to appendages (4) or to any other part on the deployment means (e.g., the inflatable balloon) (3).

According to another embodiment of the present invention, the method additionally comprising step of coupling said proximal portion (200a) of said fixating means (200) to various locations on said deployment means (e.g., the inflatable balloon) (3), thus accommodating a variety of mesh sizes.

According to another embodiment of the present invention, the method additionally comprising step of extracting said deployment means (e.g., the inflatable balloon) (3) from with in the abdominal cavity and/or pre-peritoneal and/or hollow body organs and/or natural and/or artificial orifices and/or spaces and/or post operative spaces (i.e., hernia).

According to another embodiment of the present invention, the method additionally comprising step of deflating said inflatable balloon, or minimizing the relevant segments/parts of any other deployment means.

According to another embodiment of the present invention, the method additionally comprising step of continuing inflating said inflatable balloon according to a predetermined medical need, or preserving the needed size of other deployment means.

According to another embodiment of the present invention, the method additionally comprising step of fitting the center of said deployment means (e.g., the inflatable balloon) to the center of said hernia or any desired position in the abdominal cavity and/or said pre-peritoneal and/or said hollow body organs and/or said natural and/or said artificial orifices and/or said spaces and/or said post operative spaces.

According to another embodiment of the present invention, the method additionally comprising step of threading centering means (5) through said mesh.

According to another embodiment of the present invention, the method additionally comprising step of ensuring that the right side and the right direction of said mesh is directed to said hernia, or to abdominal cavity and/or said pre-peritoneal and/or said hollow body organs and/or said natural and/or said artificial orifices and/or said spaces and/or said post operative spaces.

According to another embodiment of the present invention, the method additionally comprising step of selecting the shape of said deployment means (or specifically the inflatable balloon) from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, an H-like shape, a grid-like shape, a flat structure, a 3D structure and a rake-like shape or any combination thereof.

It should further emphasized that different deployment means can be used. Although the above disclosure is related to a specific deployment means (i.e., an inflated balloon), the fixating means 200 can utilized to any deployment, means available.

FIG. 9b illustrates in a flowchart for a method (700) for attaching a mesh to deployment means according to a preferred embodiment of the fixating means. The method comprises steps of obtaining (step 702) a hernia kit comprising:

i. a mesh (2);

ii. at least one deployment means (3), adapted to deploy said mesh with in the abdominal cavity and/or pre-peritoneal and/or hollow body organs and/or natural and/or artificial orifices and/or spaces and/or post operative spaces; and, iii. fixating means (200) coupled to said deployment means (3), adapted to attach said deployment means (3) to said mesh (2); said fixating means are characterized by at least two portions:

a. a first (proximal) portion (200a) firmly coupled to said deployment means (3);

b. a second (middle) portion (200b), comprising a coil (252) having a predetermined retracted shape; said coil is reconfigurable from a plurality of unretracted positions to a plurality of retracted positions and from said plurality of retracted positions to said plurality of unretracted positions;

The next step (step 703) is to obtain attaching means adapted to thread said second portion (200b) through said mesh (2).

Next, (step 704) the attaching means are reversibly coupled to said second portion (200b).

Then (step 705), the second portion (200b) is thread through said mesh (2) via said attaching means.

Next (step 706), the coil (252) is reconfigurable from retracted (e.g., helical) configuration into at least partially linear configuration.

Next (step 707), re-actuating the coil (252) of the fixating means (200) thus, reconfiguring said coil (252) from unretracted position (linear shape) into its retracted configuration (e.g., helical configuration).

Then, (step 708) the attaching means can be uncoupled from said second portions.

It should be emphasized that it is optionally to detach also the linear part (254) of fixating means (200) from the coil (252).

Once the attaching means are removed, the mesh (which is attached to the deployment means (e.g., an inflatable balloon) is adjusted and inserted into the abdominal cavity and/or pre-peritoneal and/or hollow body organs and/or natural and/or artificial orifices and/or spaces and/or post operative spaces.

According to one embodiment of the present invention, the deployment means are an inflatable balloon. However, it should be emphasized that the above mentioned method can be employed on any deployment means and it should not be restricted to an inflatable balloon.

According to another embodiment of the present invention, the retracted shape of the coil (252) is at least partially helical and/or spiral.

According to another embodiment of the present invention, the method additionally comprising step of inflating at least a portion of said inflatable balloon or actuating only part of the other deployment means, thereby spreading and/or deploying said mesh.

According to another embodiment of the present invention, the method as described above additionally comprising step of adjusting said mesh attached to said deployment means (e.g., the inflatable balloon) and inserting said adjusted deployment means attached to said mesh into the abdominal cavity and/or pre-peritoneal and/or hollow body organs and/or natural and/or artificial orifices and/or spaces and/or post operative spaces.

According to another embodiment of the present invention, the method additionally comprising step of coupling said fixating means (200) to said deployment means (e.g., the inflatable balloon) (3) by means selected from a group consisting of glue, Velcro, mechanical connections selected from a group consisting of a disc or a knot), welding proximal portion (200a) to the appendages (4), threading said fixating means through the appendages (4) or through holes in the appendages (4) or through any other part of the deployment means or any combination thereof.

According to another embodiment of the present invention, said step (e) of reconfiguring said coil from said retracted position to an unretracted position additionally comprising step of mechanically pulling said coil.

According to another embodiment of the present invention, said step (f) of reconfiguring said coil unretracted position to said retracted position additionally comprising step of releasing said mechanical stress.

According to another embodiment of the present invention, said step (e) or said step (f) of reconfiguring said coil is performed by means selected from a group consisting of application of electrical current on said coil, thermoregulating said coil, application of magnetic field on said coil.

According to another embodiment of the present invention, said step (I) of reconfiguring said coil unretracted position to said retracted position is performed spontaneously.

According to another embodiment of the present invention, the method additionally comprising step of selecting said coil to have more than one coiling radius.

According to another embodiment of the present invention, the method additionally comprising step of selecting said attaching means from sharpened element selected from a group consisting of a stylet or a needle.

According to another embodiment of the present invention, the method additionally comprising step of coupling said first portion of said fixating means (200) to appendages on said deployment means (e.g., the inflatable balloon) (3).

According to another embodiment of the present invention, the method additionally comprising step of coupling said first portion (200a) of said fixating means (200) to various locations on said deployment means (e.g., the inflatable balloon) (3), thus accommodating a variety of mesh sizes.

According to another embodiment of the present invention, the method additionally comprising step of extracting said deployment means (e.g., the inflatable balloon) from said hernia.

According to another embodiment of the present invention, the method additionally comprising step of deflating said inflatable balloon, or minimizing the relevant segments/parts of any other deployment means.

According to another embodiment of the present invention, the method additionally comprising step of continuing inflating said inflatable balloon or preserving the needed size of other deployment means, according to a predetermined medical need. According to another embodiment of the present invention, the method additionally comprising step of fitting the center of said inflatable balloon or other deployment means, to the center of said hernia or any desired position in said abdominal cavity and/or said pre-peritoneal and/or said hollow body organs and/or said natural and/or said artificial orifices and/or said spaces and/or said post operative spaces.

According to another embodiment of the present invention, the method additionally comprising step of threading centering means (5) through said mesh.

According to another embodiment of the present invention, the method additionally comprising step of ensuring the right side of said mesh is directed to said hernia or to abdominal cavity and/or said pre-peritoneal and/or said hollow body organs and/or said natural and/or said artificial orifices and/or said spaces and/or said post operative spaces.

According to another embodiment of the present invention, the method additionally comprising step of selecting the shape of said deployment means (or specifically the inflatable balloon) from a group comprising a polygonal shape, a curved shape, a symmetrical, a non-symmetrical shape, a linear shape, continues, non-continues, a concave shape, a irregular shape, a square-like shape, a rectangular shape, an oval shape, a U-like shape, an H-like shape, a grid-like shape, a flat structure, a 3D structure and a rake-like shape or any combination thereof.

Reference is now made to FIGS. 10*a* and 10*b* illustrating another embodiment of the hernia kit.

According to said embodiment the deployment means (e.g., the inflatable balloon) additionally comprises at least one clip/slit (10) adapted to grab a suture.

FIG. 10*b* illustrates a balloon (3) as the deployment means, a mesh (2), a clip/slit (10) and a suture (20) running through said mesh and grabbed in said clip. Thus, creating an attachment between said balloon and said mesh.

FIG. 11 illustrates a mesh (2) coupled to the deployment means (and specifically an inflatable balloon) via said sutures (20).

As described above, it should be emphasized that the present invention can be used in any deployment means and not limited to an inflatable balloon.

Figure 12A:
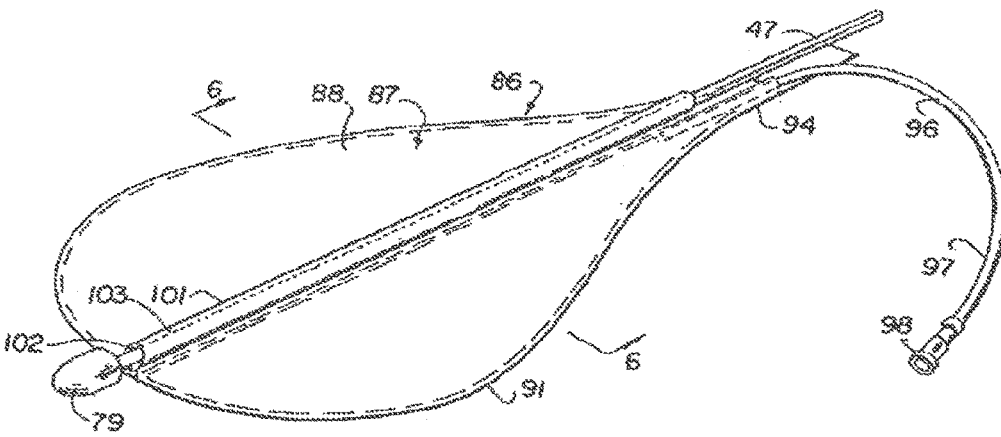
FIGS. 12A-12B schematically represent another patch/mesh deployment means.
Figure 12B:
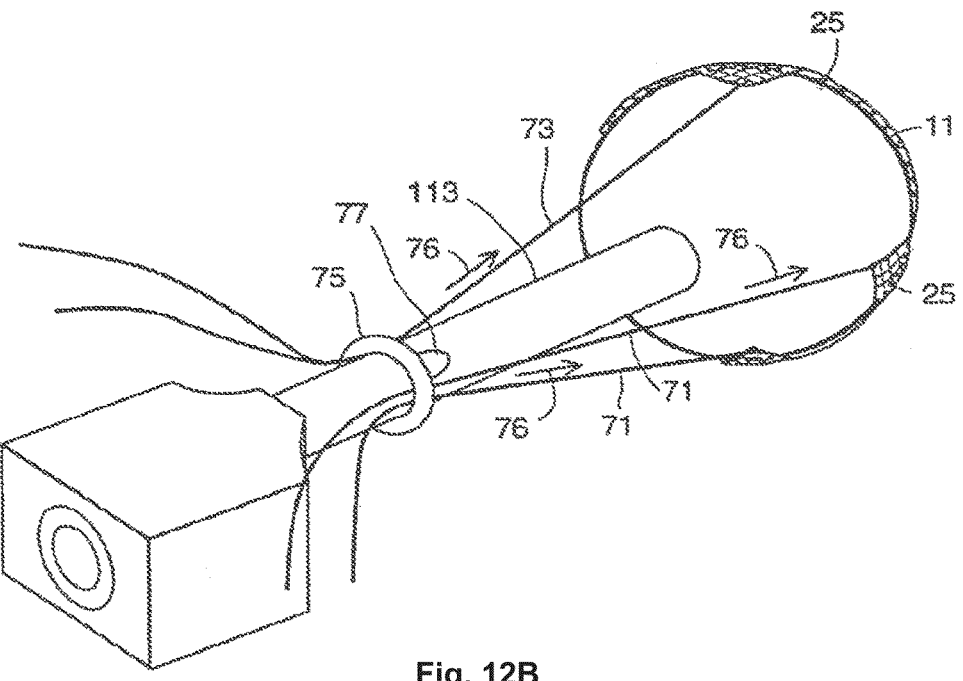

FIGS. 12*a* and 12*b* illustrates, in a non-limiting manner, another deployment means which is described in US application no. US2001/0053919 and in PCT application no. WO95/30374 respectfully. The attachment means (200) as described in the present invention can be used, for example, in the deployment means described and claimed in US application no. US2001/0053919 and in PCT application no. WO95/30374.

FIGS. 13*a* to FIG. 13*e* illustrate another deployment means, wherein said deployment means is rigid.

Figure 13A:
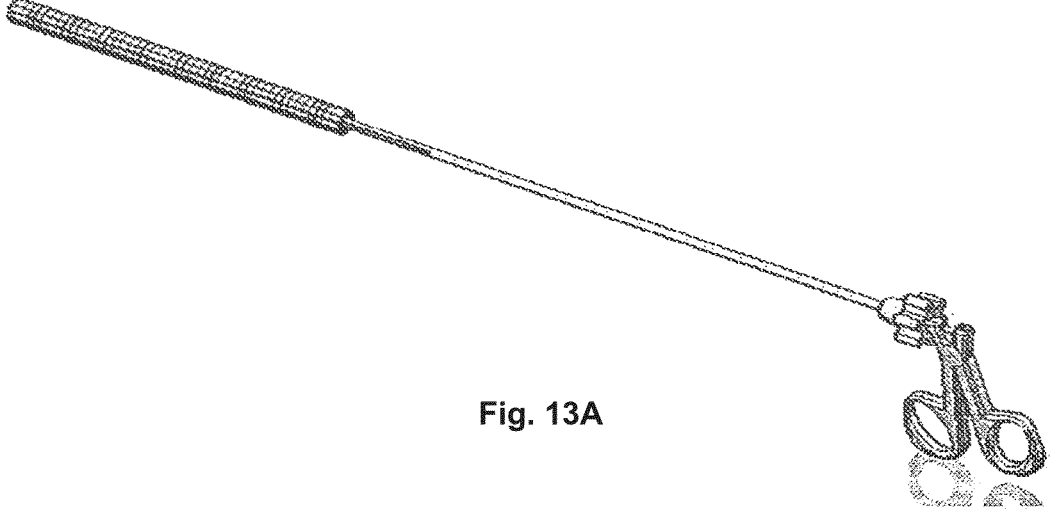
FIGS. 13A-13C schematically represent an example of a rigid patch/mesh deployment means.

FIG. 13*a* illustrates the mesh deployment means in which the mesh is adjusted.

Figure 13B:
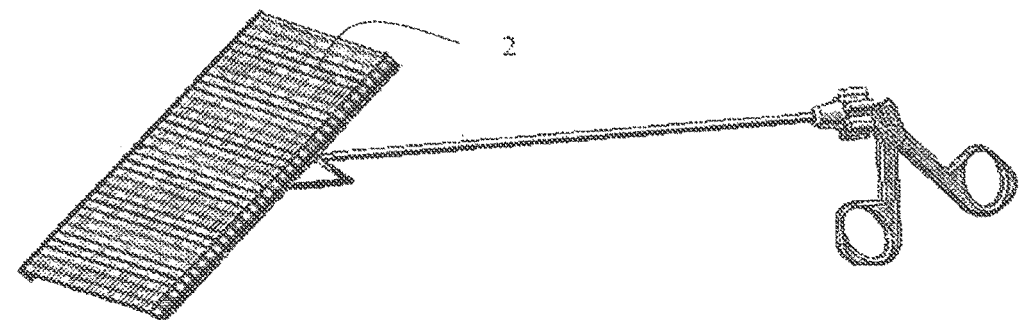

FIG. 13*b* illustrates the mesh deployment means in which the mesh is partially spread.

Figure 13C:
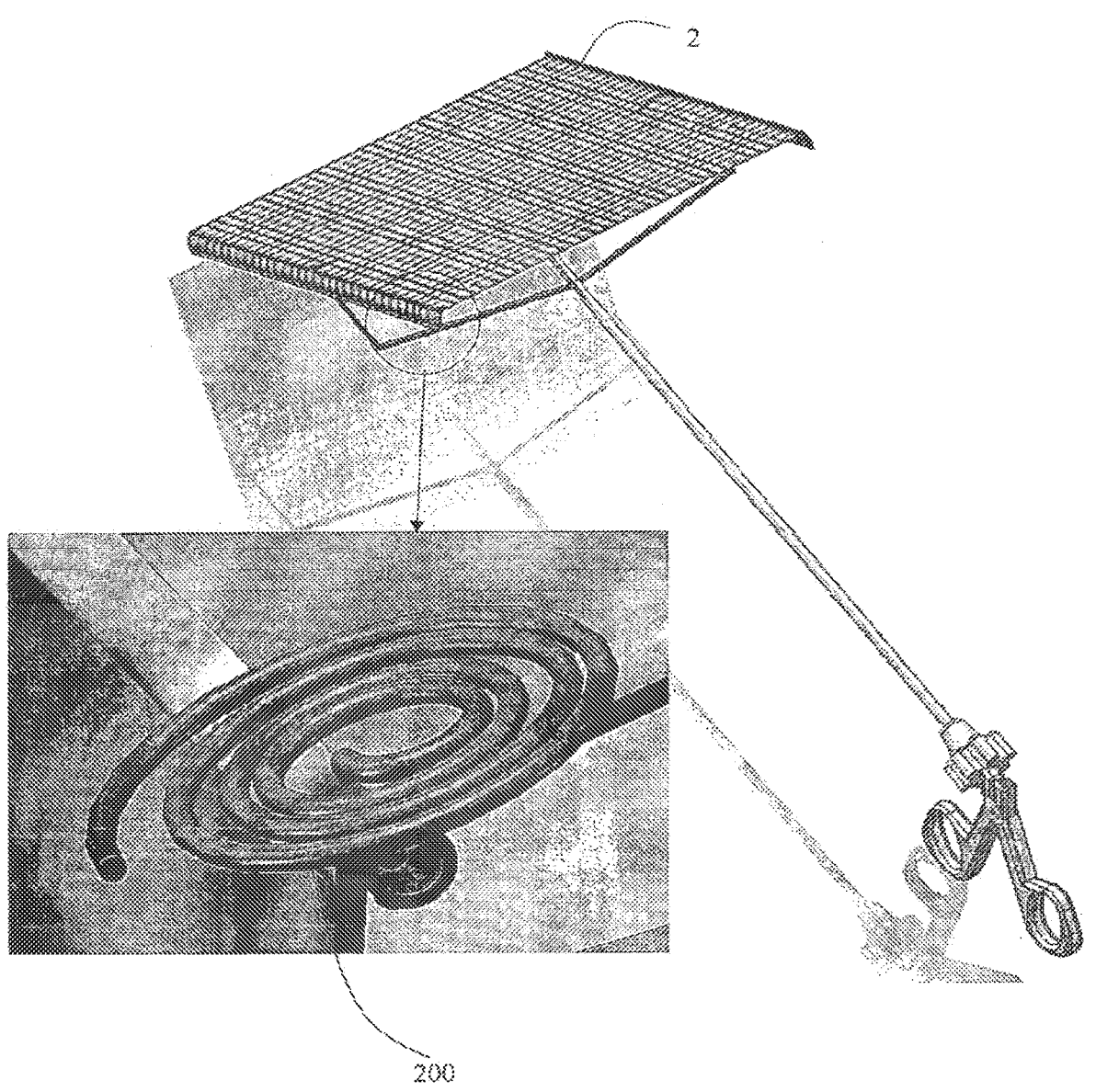

FIG. 13*e* illustrates the mesh deployment means in which the mesh is fully spread. FIG. 13*c* also illustrates the use of the fixating means 200 to attach the mesh and the mesh deployment means.

As described above, the fixating means 200 can be used in all kinds of deployment, means, including the deployment means illustrated in FIG. 13.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for delivering a soft tissue repair prosthetic, comprising:

a deployment device configured to deploy the soft tissue repair prosthetic within a body of a patient;

an appendage attached to the deployment device; and a fixating component configured to attach the soft tissue repair prosthetic to the deployment device, wherein the fixating component is coupled to the appendage, wherein the deployment device has a reduced configuration for delivering the soft tissue repair prosthetic to a placement site within the patient and an expanded configuration for deploying the soft tissue repair prosthetic, and wherein the appendage extends from an inner edge of the deployment device.

2. The device of claim 1, wherein the fixating component is coupled to the appendage by at least one of: glue, hook and loop fasteners, a weld, or a threaded arrangement.

3. The device of claim 1, wherein the appendage is formed integrally with the deployment device.

4. The device of claim 1, wherein the appendage includes at least one aperture configured to receive a portion of the fixating component.

5. The device of claim 4, wherein the at least one aperture is a through hole extending through the appendage.

6. The device of claim 1, wherein the fixating component includes an anchor component, and wherein the appendage is coupled with the anchor component.

7. The device of claim 6, wherein the appendage encapsulates the anchor component.

8. The device of claim 6, wherein the appendage is coupled with the anchor component such that the anchor component is disposed on a first side of the appendage and a second portion of the fixating component is disposed on a second side of the appendage, opposite the first side.

9. The device of claim 1, wherein the inner edge of at an outer portion of the deployment device.

10. The device of claim 9, wherein the appendage extends from the inner edge of the outer portion towards a central axis of the deployment device.

11. The device of claim 10, wherein the appendage comprises a first appendage, and the device further comprises a second appendage, wherein the first appendage extends towards the second appendage.

12. The device of claim 11, wherein the first appendage and the second appendage are disposed symmetrically with respect to the central axis.

13. The device of claim 1, wherein the appendage extends from a corner of the deployment device.

14. The device of claim 13, wherein the appendage comprises a first appendage, and the device further comprises a second appendage, a third appendage, and a fourth appendage, each of the second, third, and fourth appendages extending from a respective corner of the deployment device.

15. The device of claim 1, wherein the deployment device has a first axis extending along a length of the deployment device and a second axis extending along a width of the deployment device, and wherein the appendage comprises a first appendage, and the device further comprises a second appendage, a third appendage, and a fourth appendage, wherein the first, second, third, and fourth appendages are disposed symmetrically with respect to both the first and second axes of the deployment device.

16. The device of claim 1, wherein the deployment device comprises an inflatable balloon.

17. The device of claim 1, wherein the fixating component comprises a coil.

18. A device for delivering a soft tissue repair prosthetic, comprising:

a deployment device configured to deploy the soft tissue repair prosthetic within a body of a patient;

an appendage attached to the deployment device; and a fixating component configured to attach the soft tissue repair prosthetic to the deployment device, wherein the fixating component is coupled to the appendage, wherein the deployment device has a reduced configuration for delivering the soft tissue repair prosthetic to a placement site within the patient and an expanded configuration for deploying the soft tissue repair prosthetic, and wherein the deployment device is substantially planar in the expanded configuration, and wherein the appendage is substantially coplanar with the deployment device in the expanded configuration.

19. A device for delivering a soft tissue repair prosthetic, comprising:

a deployment device configured to deploy the soft tissue repair prosthetic within a body of a patient;

an appendage attached to the deployment device; and a fixating component configured to attach the soft tissue repair prosthetic to the deployment device, wherein the fixating component is coupled to the appendage, wherein the deployment device has a reduced configuration for delivering the soft tissue repair prosthetic to a placement site within the patient and an expanded configuration for deploying the soft tissue repair prosthetic, and wherein the appendage comprises a first appendage, and the device further comprises a second appendage, wherein the first appendage and the second appendage are disposed symmetrically with respect to a central axis of the deployment device.

20. The device of claim 19, further comprising a third appendage and a fourth appendage disposed symmetrically with respect to the central axis.

*   *   *   *   *